(12) United States Patent
Lee et al.

(10) Patent No.: US 7,915,383 B2
(45) Date of Patent: Mar. 29, 2011

(54) **METHOD OF SEPARATING A PEPTIDOGLYCAN RECOGNITION PROTEIN FROM A HEMOLYMPH *TENEBRIO MOLITOR* LARVAE**

(75) Inventors: Bok-Luel Lee, Busan (KR); Ji-Won Park, Busan (KR); Byung-Rok Je, Busan (KR); Nam-Chul Ha, Busan (KR)

(73) Assignee: Yuhan Corporation, Seoul (KR)

( * ) Notice: Subject to any disclaimer, the term of this patent is extended or adjusted under 35 U.S.C. 154(b) by 184 days.

(21) Appl. No.: 12/160,704

(22) PCT Filed: Jan. 13, 2006

(86) PCT No.: PCT/KR2006/000154
§ 371 (c)(1),
(2), (4) Date: Jul. 11, 2008

(87) PCT Pub. No.: WO2007/081067
PCT Pub. Date: Jul. 19, 2007

(65) Prior Publication Data
US 2008/0312408 A1    Dec. 18, 2008

(51) Int. Cl.
*C07K 1/00* (2006.01)
(52) U.S. Cl. ........................................... 530/350
(58) Field of Classification Search .................. None
See application file for complete search history.

(56) References Cited

OTHER PUBLICATIONS

Park et al. "A synthetic peptidoglycan fragment as a competitive inhibitor of the melanization cascade", JBC, 2006, 281(12):7747-7755.*
International Search Report and Written Opinion dated Sep. 28, 2006.
M. Zhao, et al.: "A Novel 43-kDA Protein as a Negative Regulatory Component of Phenoloxidase-induced Melanin Synthesis," J. Biol. Chem., vol. 280, No. 26, pp. 24744-24751, Jul. 1, 2005.
R. Zhang, et al.: "Characterization and Properties of a 1,3-β-D-Glucan Pattern Recognition Protein of *Tenebrio molitor* Larvae That Is Specifically Degraded by Serine Protease during Prophenoloxidase Activation," J. Biol. Chem., vol. 278, No. 43, pp. 42072-42079, Oct. 24, 2003.
M. Lee, et al.: "Peptidoglycan Recognition Proteins Involved in 1,2-β-D-Glucan-dependent Prophenoloxidase Activation System of Insect," J. Biol. Chem., vol. 279, No. 5, pp. 3218-3227, Jan. 30, 2004.
S. Lee, et al., "In vitro activation of pro-phenol-oxidase by two kinds of pro-phenol-oxidase-activating factors isolated from hemolymph of coleopteran, *Holotrichia diomphalia* larvae," Eur. J. Biochem., vol. 254, pp. 50-57, 1998.
S. Piao, et al.: "Overexpression and preliminary X-ray crystallographic analysis of prophenoloxidase activating factor II, a clip domain family of serine proteases," Biochimica et Biophysica Acta, vol. 1752, pp. 103-106, 2005.
M. Carroll, et al.: "Linkages of innate and adaptive immunity," Current Opinion in Immunology, vol. 10, pp. 36-40, 1998.
R. Medzhitov, et al.: "Innate Immunity: The Virtues of a Nonclonal System of Recognition," Cell, vol. 91, pp. 295-298, Oct. 31, 1997.
R. Medzhitov, et al.: "A human homologue of the *Drosophila* Toll protein signals activation of adaptive immunity," Nature, vol. 388, pp. 394-397, Jul. 24, 1997.
D. Hultmark: "Ancient relationships," Nature, vol. 367, pp. 116-117, Jan. 13, 1994.
S. Wasserman: "A Conserved Signal Transduction Pathway Regulating the Activity of the rel-like Proteins Dorsal and NF-kB," Molecular Biology of the Cell, vol. 4, pp. 767-771, Aug. 1993.
M. Ashida, et al.: "Activation of Pro-Phenoloxidase by Bacterial Cell Walls or β-1, 3-Glucans in Plasma of the Silkworm, Bombyx mori," Biochemical and Biophysical Research Communications, vol. 113, No. 2, pp. 562-568, Jun. 15, 1983.
A. Aspan, et al.: "Purification of Prophenoloxidase from Crayfish Blood Cells, and its Activation by an Endogenous Serine Proteinase," Insect Biochem, vol. 21, No. 4, pp. 363-373, 1991.
T. Kwon, et al.: "Purification and Characterization of Prophenoloxidase from the Hemolymph of Coleopteran Insect, *Holotrichia diomphalia* Larvae," Mol. Cells, vol. 7, No. 1, pp. 90-97, 1997.
S. Saul, et al.: "Prophenoloxidase Activation in the Hemolymph of *Sarcophaga bullata* Larvae," Archives of Insect Biochemistry and Physiology, vol. 7, pp. 91-103, 1988.
M. Ashida: "A Cane Sugar Factor Suppressing Activation of Prophenoloxidase in Haemolymph of the Silkworm, *Bombyx mori*," Insect Biochem., vol. 11, pp. 57-65, 1981.
A. Pye: "Microbial activation of prophenoloxidase from immune insect larvae," Nature, vol. 251, pp. 610-613, Oct. 18, 1974.
S. Saul, et al.: "Protease Mediated Prophenoloxidase Activation in the Hemolymph of the Tobacco Hornworm, *Munduca sexta*," Archives of Insect Biochemistry and Physiology, vol. 5, pp. 1-11, 1987.
K. Fujimoto, et al.: "Nucleotide sequence of the cDNA encoding the proenzyme of phenol oxidase Al of *Drosophila melanogaster*," Proc. Natl. Acad. Sci USA, vol. 92, pp. 7769-7773, Aug. 1995.
T. Kawabata, et al.: "Molecular cloning of insect pro-phenol oxidase: A copper-containing protein homologous to arthropod hemocyanin," Proc. Natl. Acad. Sci. USA, vol. 92, pp. 7774-7778, Aug. 1995.
S. Girardin, et al.: "Peptidoglycan Molecular Requirements Allowing Detection by Nod1 and Nod2," The Journal of Biological Chemistry, vol. 278, No. 43, pp. 41702-41708, Oct. 24, 2003.
J. Hugot, et al.: "Lessons to be learned from the NOD2 gene in Crohn's disease," European Journal of Gastroenterology & Hepatology, vol. 15, No. 6, pp. 593-597, 2003.
J. Park, et al.: "A Synthetic Peptidoglycan Fragment as a Competitive Inhibitor of the Melanization Cascade," The Journal of Biological Chemistry, vol. 281, No. 12, pp. 7747-7755, Mar. 24, 2006.
J. Park: "Purification, cDNA cloning and characterization of peptidoglycan (PGN) recognition protein and melanization inhibiting protein from *Tenebrio molitor* hemolymph," Abstract, Pusan National University, pp. 110-112, Jul. 14, 2005.
S. Inamura, et al.: "Synthetic study of peptidoglycan partial structures. Synthesis of tetrasaccharide and octasaccharide fragments," Tetrahedron Letters, vol. 42, pp. 7613-7616, 2001.
S. Inamura, et al.: "Synthesis of peptidoglycan fragments and evaluation of their biological activity," Organic & Biomolecular Chemistry, vol. 4, pp. 232-242, 2006.

* cited by examiner

*Primary Examiner* — Karen Cochrane Carlson
*Assistant Examiner* — Bin Shen
(74) *Attorney, Agent, or Firm* — Rothwell, Figg, Ernst & Manbeck, P.C.

(57) ABSTRACT

The present invention provides a separate and purified peptidoglycan-recognition protein having an amino acid sequence as set forth in SEQ ID NO: 1 and also a peptidoglycan detection kit comprising the separate and purified peptidoglycan-recognition protein.

3 Claims, 11 Drawing Sheets

A: BUFFER
B: NATURAL PGN
C: SYNTHETIC PGN OF FORMULA 1
D: SYNTHETIC PGN OF FORMULA 2
E: SYNTHETIC PGN OF FORMULA 3
F: SYNTHETIC PGN OF FORMULA 4

(A)

LSGSTIPRICPEIISRTRWGART  SEQ. ID NO.: 3

(B)

DFLQCGVELGELSK  SEQ. ID NO.: 4

NYKLFGARQVSSTSSPGLK  SEQ. ID NO.: 5

LYRELQDWPHFTRSPPK  SEQ. ID NO.: 6

FIG. 12

```
 -58    GAACTCCTGCGGTGGCGGCCGCTCTAGACTAGTGGATCCCCCGGGCTGCAGGAATTCG

1  GCACGAGGTGTGTATCAAATTTCGGCTCTCTCAGGTTCTACGATACCAAGAATATGTCCT
       A  R  G  V  Y  Q  I  S  A  L  S  G  S  T  I  P  R  I  C  P    20
  61  GAAATTATTAGTCGGACAAGATGGGGGGCGAGAACTCCATTAGAAGTGGATTATTCTTTA
       E  I  I  S  R  T  R  W  G  A  R  T  P  L  E  V  D  Y  S  L    40
 121  ATTCCCATTGAAAATGTTGTTGTTCATCATACTGTAACTCATACATGCGACTCGGAAAGC
       I  P  I  E  N  V  V  V  H  H  T  V  T  H  T  C  D  S  E  S    60
 181  GAATGTGCAACTCTTTTGAGAAATGTTCAGAATTTTCACATGGAAAACTTAGAATTTCAT
       E  C  A  T  L  L  R  N  V  Q  N  F  H  M  E  N  L  E  F  H    80
 241  GACATAGGATACAACTTTTTGGTTGCAGGTGACGGACAAATATACGAAGGAGCGGGTTGG
       D  I  G  Y  N  F  L  V  A  G  D  G  Q  I  Y  E  G  A  G  W   100
 301  CATAAAGTTGGAGCGCATACCAGAGGCTACAATACAAGATCCTTGGGATTAGCCTTTATT
       H  K  V  G  A  H  T  R  G  Y  N  T  R  S  L  G  L  A  F  I   120
 361  GGCAACTTCACAAGCCAACTACCAGTCCAAAAACAGCTTAAAGTTGCTAAAGATTTTCTT
       G  N  F  T  S  Q  L  P  V  Q  K  Q  L  K  V  A  K  D  F  L   140
 421  CAATGCGGAGTTGAACTGGGAGAATTAAGTAAAAATTATAAATTATTTGGAGCACGCCAA
       Q  C  G  V  E  L  G  E  L  S  K  N  Y  K  L  F  G  A  R  Q   160
 481  GTGAGTTCGACAAGCAGCCCTGGACTGAAACTCTACCGTGAACTGCAAGATTGGCCCCAT
       V  S  S  T  S  S  P  G  L  K  L  Y  R  E  L  Q  D  W  P  H   180
 541  TTCACCAGATCTCCTCCTAAATAAATTCATCAACAGTTCAACAATTGTTGTATTTTATAT
       F  T  R  S  P  P  K  *   SEQ. ID NO.: 11 – amino acid sequence  188
 601  TATTGTTTTATGTCATTAAATAATCGAATTATCGGGCGGAGGCCAAAAAATAGACATAAA

661  ATACACGCAGGCATAAAAACACAGACAAACAAAAAAATTTTCTCGAGTGGGAGCCCGGT

721  ACCAATTACGCCCTATAGTGAGTCGTATAACAGATTCACTGGGCGGTCGTTTTACACGTG

781  CGTGACTGGGAAAAACCCTTG        SEQ. ID NO.: 10 – cDNA sequence
```

METHOD OF SEPARATING A PEPTIDOGLYCAN RECOGNITION PROTEIN FROM A HEMOLYMPH *TENEBRIO MOLITOR* LARVAE

CROSS REFERENCE TO RELATED APPLICATIONS

This application is a 35 USC §371 National Phase Entry Application from PCT/KR2006/000154, filed Jan. 13, 2006, and designating the United States.

TECHNICAL FIELD

The present invention relates to a method of separating a peptidoglycan-recognition protein from the hemolymph of *Tenebrio molitor* larvae using synthetic peptidoglycan, a peptidoglycan-recognition protein separated using the method, a polynucleotide encoding the peptidoglycan-recognition protein, and a kit including the peptidoglycan-recognition protein.

BACKGROUND ART

Most living organisms are under constant assault from external harmful environmental factors such as pathogens and parasites, but can defend themselves against the harmful environmental factors due to their immune systems. Immune systems are divided into innate and adaptive immune systems according to how to recognize an external foreign substance. In contrast to invertebrates that have only an innate immune system, vertebrates, such as humans, have both an innate immune system and an adaptive immune system. An adaptive immune system, observed only in vertebrates, is a memory-dependent immune system that induces a continued immune response by recognizing respective structures of harmful foreign substances (so-called antigens) that have invaded the body and selectively creating antibodies specific to the antigens. On the other hand, an innate immune system, observed in both of vertebrates and invertebrates, is a memory-independent immune system that recognizes and quickly responds to a conserved element (i.e., a pattern) shared among pathogens. Up until several years ago, the innate immune system was recognized as a less specific, less developed defense mechanism than the adaptive immune system, which primarily protects the body from an invading foreign substance until the latter generates antibodies.

However, active research into the immune system at the molecular level has been performed in recent years, and it has been determined that the innate immune system plays a critical role in the activation of the adaptive immune system [Carroll, M. C. et al, *Curr. Opin. Immunol.* 10, 36-48 (1998); Ruslan, M. et al., *Cell* 91, 295-298 (1997)], bringing the importance of the innate immune system into prominence.

These facts suggest that the regulation of the innate immune system could lead to a change in the adaptive immune system. Thus, new conceptual approaches to the innate immune system are required in terms of the treatment of diseases and the development of new drugs. Recently, the innate immune system has been actively studied at the molecular level by many domestic and foreign researchers [Medzhitov, R. et al., *Nature* 388, 394-397 (1997)].

Research into the innate immune system has been conducted mainly using invertebrates having an innate immune system. In particular, insects have been used in many researches on the innate immune system. Recent research results at the to molecular level show that there are similarities between the innate immune system in insects and that in humans, and thus, research into the innate immune system has been actively done using various insects. [Medzhitov, R. et al., (1997) *Nature* 388, 394-397 (1997); Hultmark, D. (1994), *Nature* 367, 116-117 (1994); Wasserman, S. A. *Mol. Biol. Cell.* 4, 767-771 (1993)].

The immune system of insects can be divided into a cellular immune response and a humoral immune response. The humoral immune response includes the secretion of antibacterial proteins into the body fluid against the invasion of foreign substances, the induction of lectin recognizing a specific sugar in invaded foreign substances, the activation of pro-phenoloxidase (hereinafter, referred to as "pro-PO") known to be associated with melanin production and others.

According to research results on the pro-PO activation system in insects, it has been found that a serine proteinase inhibitor selectively inhibits the activity of phenoloxidase (PO) [Ashida, M. et al., *Biochem. Biophys. Res. Commun.* 113, 562-568 (1983)]. It has been reported that pro-PO is activated by a pro-PO cascade mediated by pro-PO activating factors (PPAFs) having a serine proteinase property [Aspan, A et al., *Insect Biochem.*, 21, 363-373 (1991)]. It has also been reported that the pro-PO cascade mediated by PPAFs is initiated by a so-called pattern such as beta-1,3-glucan which is a fungal cell wall constituent [Kwon, T. H. et al., *Mol. Cells.* 7, 90-97 (1997); Saul, S. et al., *Archs. Insect Biochem. Physiol.* 7, 91-103 (1988); Ashida, M., *Bombyxi mori, Insect Biochem.* 11, 57-65 (1981)], or lipopolysaccharide (LPS) and peptidoglycan (PGN) which are bacterial cell wall constituents [Saul, S. et al., *Archs. Insect Biochem. Physiol.* 7, 91-103 (1988); Ashida, M., *Bombyxi mori, Insect Biochem.* 11, 57-65 (1981); Pye, A. E., *Nature* 251, 610-613 (1974)].

Generally, PO exists as inactive proenzyme (zymogen). When activated, PO catalyzes the oxidation of diphenols to quinones to thereby produce melanin. It is known that PO contains a copper in its molecule. In particular, it is thought that PO of insects plays a critical role in defense mechanisms such as browning and sclerotization of insect cuticles, leakage of body fluid from a wound site for wound healing, and protection of the body against invasive pathogens.

Pro-PO associated with defense mechanisms of insects had been actively studied by many researchers for the past several decades, but had not been isolated, purified, or sequenced until pro-PO from the larvae of three insects, *Drosophila melanogaster, Bombyx mori*, and tobacco hornworm (*Manduca sexta*) was isolated and purified, and its amino acid sequence was determined in 1995 [Saul S. et al., *Archs. Insect Biochem. Physiol.*, 5, 1-11 (1987); Fujimoto K. et al., *PNAS,* 92, 7769-7773; Kawabata T. et al., *PNAS,* 92, 7774-7778 (1995)].

Natural pattern-recognition proteins involved in the innate immune system of is insects have been identified, and their biological functions in the pro-PO cascade have been partially identified [Girardin S E, et al., *J Biol. Chem.* 278: 803283 (2003); Hugot J P et al., *Curr Opin Immunol.* 15: 593597 (2003)]. Furthermore, β-1,3-glucan-recognition proteins have been isolated and identified from the hemolymph of the larvae of *Tenebrio molitor* belonging to order Coleoptera, and the relationship between the β-1,3-glucan-recognition proteins and the pro-PO cascade has been reported. In addition, β-1,3-glucan-recognition proteins have been isolated and identified from the hemolymph of larvae of *Holotrichia diomphalia* (Korean black chafer), and the biological functions of the β-1,3-glucan-recognition proteins have been reported [Lee M H, et al., *J Biol. Chem.* 279(5): 3218-27 (2000); Zhang R et al., *J Biol. Chem.* 278(43):42072-9. (2003)].

Recently, it has been reported that, among the identified pattern-recognition proteins, PGN-recognition proteins (PGRPs) isolated from the hemolymph of *Holotrichia diomphalia* larvae specifically recognize β-1,3-glucan, which is a fungal pattern, not PGN, and activate the pro-PO cascade [Lee M H, et al., *J Biol. Chem.* 279(5):3218-27 (2000)]. This shows that the relationship between the molecular mechanism of natural pattern-recognition proteins and the activation mechanism of the pro-PO cascade is yet to be identified.

It has been reported that the pro-PO cascade of the hemolymph of *Tenebrio molitor* larvae is activated by β-1,3-glucan, which is a fungal pattern. It has also been found that proteins specifically recognizing β-1,3-glucan are present in the hemolymph of *Tenebrio molitor* larvae. These results open new possibilities for the development of diagnostic reagents for detecting fungal infections [Zhang R et al., *J Biol. Chem.* 278(43):42072-9. (2003)].

A PO activation system, which includes a cascade pathway for PO activation, is easily triggered by internal factors activated in response to the invasion of pathogens or foreign substances or the degranulation of host blood cells, converting pro-PO to PO to thereby produce melanin from catecholamines. Thus, it is difficult to separate pattern-recognition proteins that specifically recognize patterns (such as PGN and (β-1,3-glucan) triggering the PO activation system.

BRIEF DESCRIPTION OF THE DRAWINGS

The above and other features and advantages of the present invention will become more apparent by describing in detail exemplary embodiments thereof with reference to the attached drawings in which:

FIG. 12 shows the sequence of cDNA encoding a 20 kDa PGN-recognition protein (SEQ ID NO: 10) and the sequence of amino acids expressed from the cDNA (SEQ ID NO: 11).

DETAILED DESCRIPTION OF THE INVENTION

Technical Goal of the Invention

Figure 1:
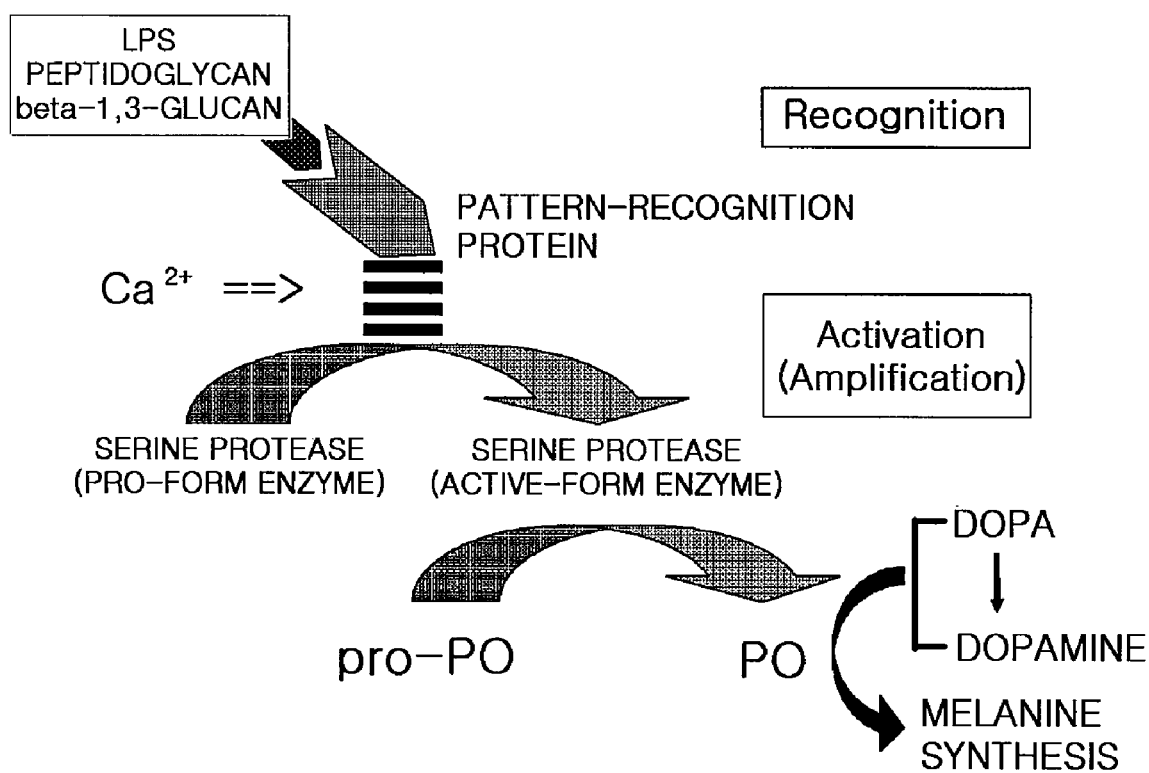
FIG. 1 is a schematic diagram illustrating a phenoloxidase (PO) activation system.

In view of the above problems, the present inventors developed a method of separating a peptidoglycan (PGN)-recognition protein involved in a phenoloxidase (PO) activation system from the hemolymph of *Tenebrio molitor* larvae using synthetic PGN that can bind with the PGN-recognition protein but cannot activate the subsequent cascade of PO activation.

Therefore, the present invention provides a method of separating a PGN-recognition protein from the hemolymph of *Tenebrio molitor* larvae using synthetic PGN.

The present invention also provides a method of separating pattern-recognition protein fractions except a PGN-recognition protein from the hemolymph of *Tenebrio molitor* larvae.

The present invention also provides a PGN-recognition protein separated using the method and a polynucleotide encoding the PGN-recognition protein.

The present invention also provides a PGN detection kit including the PGN-recognition protein.

DISCLOSURE OF THE INVENTION

According to an aspect of the present invention, there is provided a method of separating a peptidoglycan (PGN)-recognition protein from the hemolymph of *Tenebrio molitor* larvae, the method including: (a) preparing an affinity chromatography column by packing a column with a resin bound with at least one synthetic PGN selected from the group consisting of compounds represented by Formulae 1-4 below; (b) applying the hemolymph of *Tenebrio molitor* larvae to the affinity chromatography column; (c) applying a mobile phase to the affinity chromatography column to obtain a PGN-recognition protein-containing solution eluted from the affinity chromatography column; and (d) purifying a PGN-recognition protein from the eluted solution:

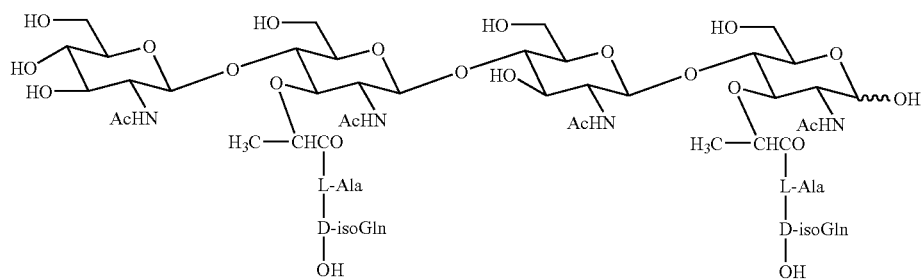

<Formula 1>

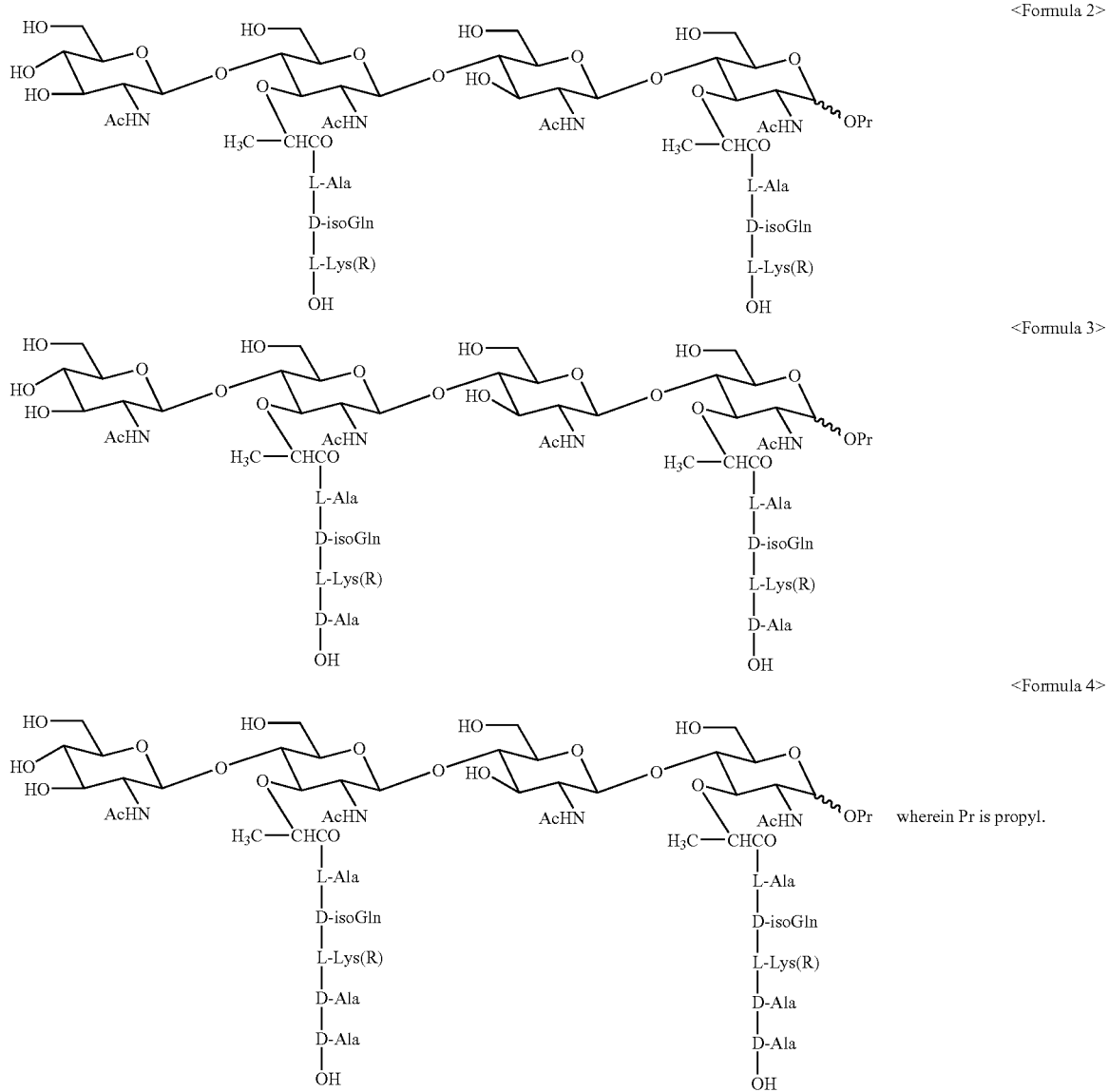

According to another aspect of the present invention, there is provided a method of separating pattern-recognition protein fractions except a PGN-recognition protein from the hemolymph of *Tenebrio molitor* larvae, the method including: (a) preparing an affinity chromatography column by packing a column with a resin bound with at least one synthetic PGN selected from the group consisting of the compounds represented by the above Formulae 1-4; (b) applying the hemolymph of *Tenebrio molitor* larvae to the affinity chromatography column; (c) applying a washing solution to the affinity chromatography column to obtain a solution of other pattern-recognition proteins but PGN-recognition proteins eluted from the affinity chromatography column; and (d) purifying fractions of the pattern-recognition proteins except PGN-recognition proteins from the eluted solution.

According to a further aspect of the present invention, there are provided a PGN-recognition protein separated using the method, and a polynucleotide encoding the PGN-recognition protein.

According to yet another aspect of the present invention, there is provided a PGN detection kit including the PGN-recognition protein.

BEST MODE FOR CARRYING OUT THE INVENTION

The present invention will now be described more fully with reference to the accompanying drawings, in which exemplary embodiments of the invention are shown.

The present invention provides a method of separating a peptidoglycan (PGN)-recognition protein from the hemolymph of *Tenebrio molitor* larvae using synthetic PGN. The synthetic PGN is selected from the group consisting of compounds represented by Formulae 1-4 below, the compound of Formula 3 being preferred:

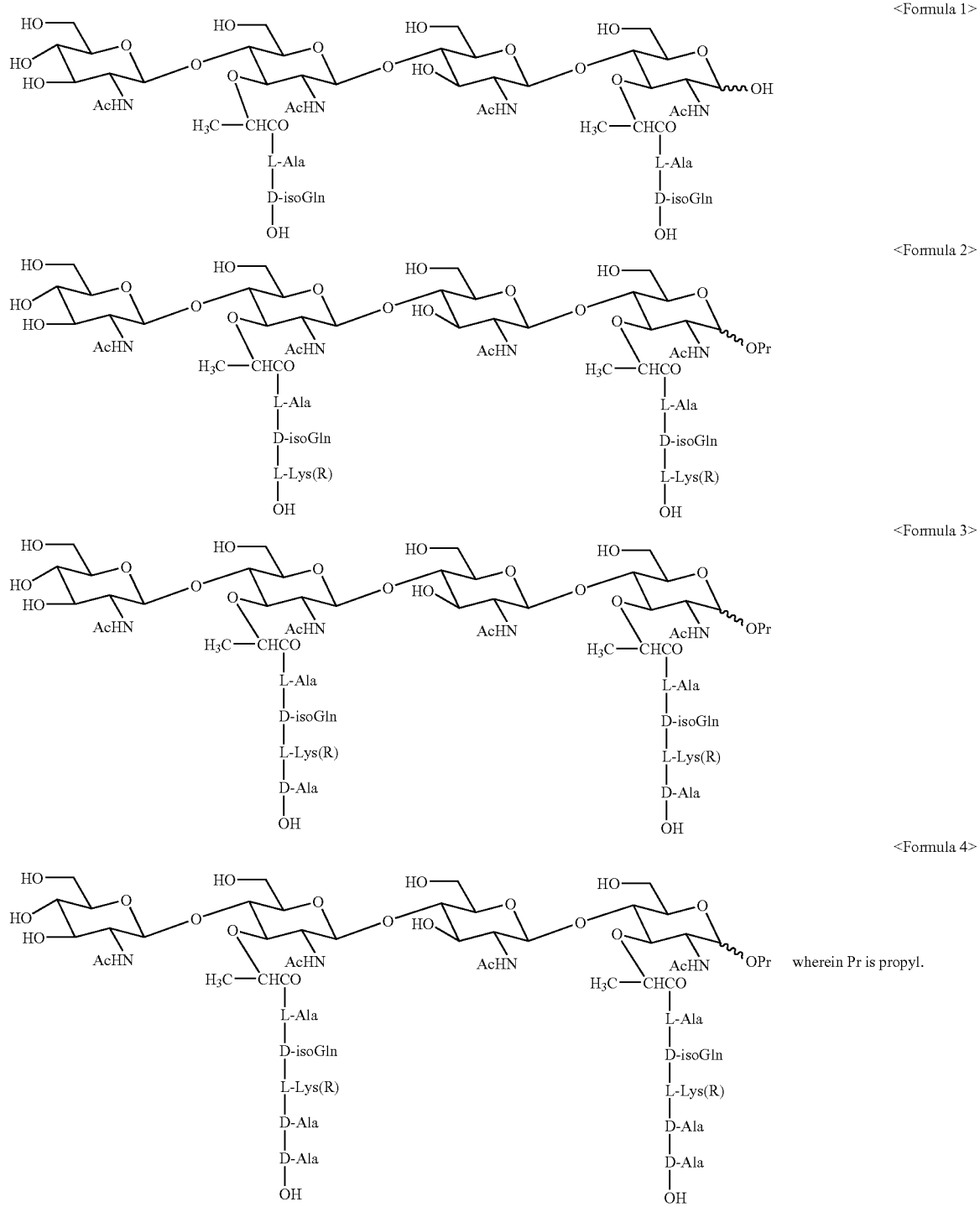

The synthetic PGN has a similar structure to that of natural PGN of gram-positive bacteria. The synthetic PGN and the natural PGN competitively bind to a PGN-recognition protein. That is, the synthetic PGN can bind to the PGN-recognition protein but cannot activate the subsequent cascade for phenoloxidase (PO) activation. Thus, the synthetic PGN serves as a competitive inhibitor of the natural PGN.

The method of separating the PGN-recognition protein according to the present invention includes preparing an affinity chromatography column by packing a column with a resin bound with at least one synthetic PGN selected from the group consisting of is the compounds represented by the above Formulae 1-4. The resin may be Sepharose, Sephadex, etc. A Sepharose resin is preferred.

The method of separating the PGN-recognition protein according to the present invention includes applying the hemolymph of *Tenebrio molitor* larvae to the affinity chromatography column prepared as above. In this step, a PGN-recognition protein in the hemolymph of *Tenebrio molitor* larvae is bound to the synthetic PGN in the affinity chromatography column.

The method of separating the PGN-recognition protein according to the present invention includes applying a mobile phase to the affinity chromatography column to obtain a PGN-recognition protein-containing solution eluted from the affinity chromatography column. The mobile phase may be a Tris-HCl solution containing EDTA and NaCl, preferably, a 50 mM Tris-HCl solution (pH 7.5) containing 1M NaCl and 3 mM EDTA.

The method of separating the PGN-recognition protein according to the present invention includes purifying the PGN-recognition protein from the eluted solution. That is, proteins in the eluted solution from the affinity chromatography column are analyzed by SDS-PAGE, etc., and PGN-recognition protein-containing fractions, as judged by SDS-PAGE, are purified.

The purification of the PGN-recognition protein can be performed using various purification methods known in the art, e.g., size-exclusion chromatography, ion concentration gradient chromatography, ion-exchange chromatography, etc. To increase the purification efficiency of the PGN-recognition protein, the eluted solution may be concentrated prior to the purification.

According to an embodiment of the method of the present invention, the purification of the PGN-recognition protein may be performed by sequential execution of size-exclusion column chromatography, ion concentration gradient column chromatography, and ion-exchange column chromatography of the eluted solution. At this time, the size-exclusion column chromatography, the ion concentration gradient column chromatography, and the ion-exchange column chromatography may be respectively performed on a Toyopearl Hw55S column, a hydroxyapatite column, and a Mono-Q FPLC column.

The present invention also provides a method of separating pattern-recognition protein fractions except a PGN-recognition protein from the hemolymph of *Tenebrio molitor* larvae, the method including: (a) preparing an affinity chromatography column by packing a column with a resin bound with at least one synthetic PGN selected from the group consisting of the compounds represented by the above Formulae 1-4; (b) applying the hemolymph of *Tenebrio molitor* larvae to the affinity chromatography column; (c) applying a washing solution to the affinity chromatography column to obtain a solution of other pattern-recognition proteins but PGN-recognition proteins eluted from the affinity chromatography column; and (d) purifying fractions of the pattern-recognition proteins except PGN-recognition proteins from the eluted solution.

Steps (a), (b), and (d) can be performed in a similar manner to those of the above-described method of separating the PGN-recognition protein. The washing solution used in (c) may be an EDTA-containing Tris buffer (pH 6.0), preferably a 3 mM EDTA-containing 50 mM Tris buffer (pH 6.0).

The present invention also provides a PGN-recognition protein separated using the method of separating the PGN-recognition protein. According to an embodiment of the present invention, the PGN-recognition protein may have an amino acid sequence as set forth in SEQ ID NO: 1.

The present invention also provides a polynucleotide encoding the PGN-recognition protein. According to an embodiment of the present invention, the polynucleotide may have a nucleotide sequence as set forth in SEQ ID NO: 2.

The present invention also provides a kit for detecting PGN in a sample using a PGN-recognition protein derived from the hemolymph of *Tenebrio molitor* larvae.

The PGN in a sample may be derived from bacterial cell walls. Thus, the presence of bacteria in the sample can be promptly and easily detected using the kit. According to an embodiment of the present invention, the PGN-recognition protein may have an amino acid sequence as set forth in SEQ ID NO: 1.

Hereinafter, the present invention will be described more specifically with reference to the following Examples. The following Examples are for illustrative purposes and are not intended to limit the scope of the present invention.

Example 1

Extraction of Hemolymph of *Tenebrio molitor* Larvae

*Tenebrio molitor* larvae were obtained from the insectarium in Seoul Grand Park (Korea) and raised. Wheat bran and cabbage were fed to the larvae at room temperature (about 25° C.) until the larvae were grown to a size of greater than about 2 cm for use in subsequent experiments.

The larvae (average weight, 0.1 g/larva) were cryoanesthesized on ice. A 5 ml sterilized syringe equipped with a 25 G needle was filled with an anticoagulation buffer (15 mM NaCl, 83 mM trisodium citrate, 26 mM citric acid, and 20 mM EDTA; pH 5.0).

1.4 ml of the anticoagulation buffer was added to sterilized eppendorf tubes, and hemolymph secreted from the larvae by pricking the first segments of the larval heads with a needle was then put into the effendorf tubes. The hemolymph secreted from 15 larvae was collected per tube.

Example 2

Preparation of Natural PGN or β-1,3-glucan

PGNs from *S. aureus* and *M. luteus* were purchased from Fluka, and β-1,3-glucan (Curdlan) was purchased from Wako Pure Chemicals (Japan).

The PGNs from *S. aureus* and *M. luteus* were ultrasonically homogenized. The water-soluble PGNs thus-obtained were treated with a 20 mM Tris buffer (pH 8.0) to obtain a 10% PGN solution and was used in an amount of 1 μg PGN in a reaction solution.

Example 3

Preparation of Synthetic PGN (1) Preparation of allyl 6-O-benzyl-4-(3-O-benzyl-4,6-O-benzylidene-2-deoxy-2-(2,2,2-trichloroethoxycarbonylamino)-β-D-glucopyranosyl)-3-O-((R)-1-(ethoxycarbonyl)ethyl)-2-deoxy-glucopyranoside (Compound 4)

Trimethylsilyl trifluoromethanesulfonate (TMSOTf) (340 μl, 3.0 mmol) was added to a mixture of N-Troc-glucosaminyl trichloroacetimidate donor (compound 2) (26.0 g, 38 mmol), an N-muramyl receptor (compound 3) (17.0 g, 30 mmol), and membrane-spanning 4A family (MS4A) in anhydrous dichloromethane at −15° C.

TABLE 1

Chemical structure

Compound 2: [structure showing Ph, BnO, O, O, TrocNH, O-C(=NH)CCl₃]

Compound 3: [structure showing BnO, HO, O, CH₃, CH, CO₂Et, TrocNH, OAllyl]

The resultant mixture was stirred at −15° C. for 10 minutes. The reaction solution was quenched with a cooled saturated NaHCO₃ solution (30 mL) and extracted with CHCl₃ (250 mL). The organic layer was washed with NaHCO₃ (60 mL) and brine (60 mL), dried over Na₂SO₄, and concentrated in vacuo. The residue was purified by silica gel chromatography (600 g, toluene:EtOAc=10:1) to give the titled compound (29.0 mg, 88%) as a pale yellow solid:

ESI-TOF-MS (positive) m/z 1119.2 [M+Na]⁺;

$^1$H NMR (400 MHz, CDCl₃) δ=7.45-7.29 (15H, m, ($C_6H_5$)—CH₂—), 5.85-5.78 (1H, m, —CH₂—CH=CH₂), 5.57 (1H, s, Ph-CH=), 5.28-5.13 (3H, m, H-1, —CH₂—CH=CH₂), 4.89-4.59 (10H, m, CCl₃-CH₂—OCO—, CH₃—CH₂—OCO—, Ph-CH₂—), 4.43-4.39 (1H, m, H-6'), 4.26-4.04 (5H, m, Lac-αH, Ph-CH₂—, H-1'. —CH₂—CH=CH₂), 3.98-3.93 (2H, m, —CH₂—CH=CH₂, H-3), 3.77-3.56 (6H, m, H-2, H-4, H-4', H-6, H-6'), 3.43-3.41 (2H, m, H-2', H-5), 3.25-3.21 (2H, m, H-3, H-5'), 1.34-1.25 (6H, m, Lac-CH₃, CH₃—CH₂—OCO). Found: C, 51.42; H, 4.90; N, 2.60. Calcd for $C_{47}H_{54}Cl_6N_2O_{15}$: C, 51.33; H, 4.95; N, 2.55%.

(2) Preparation of disaccharide 1-O-trichloroacetoimidate (Compound 12)

A solution of the compound 4 (3.0 g, 2.7 mmol) in anhydrous THF (6 mL) was degassed, and H₂-activated [Ir(cod)(MePh₂P)₂]PF₆ (23 mg, 0.027 mmol) was added thereto. The reaction mixture was stirred at room temperature under a nitrogen atmosphere for one hour, and a solution of H₂-activated [Ir(cod)(MePh₂P)₂]PF₆ (23 mg, 0.027 mmol) in anhydrous THF (3 mL) was added thereto. The reaction mixture was stirred at room temperature under a nitrogen atmosphere for one hour, and iodine (690 mg, 2.7 mmol) and water (10 mL) were added thereto. The reaction mixture was stirred for further 10 minutes, and an aqueous solution of Na₂SO₃ (5%, 100 mL) was immediately added thereto. The resultant solution was extracted with EtOAc (50 mL). The organic layer was washed with aqueous Na₂S₂O₂ (5%, 50 mL×2), a saturated NaHCO₃ solution (100 mL×2), and brine (50 mL), dried over Na₂SO₄, and concentrated in vacuo. The residue was purified by silica gel chromatography (180 g, toluene:EtOAc=4:1) to give the titled compound (2.72 mg, 93%) as a pale yellow solid:

$[\alpha]_D^{23}$=+8.4 (c 1.00, CHCl₃);

ESI-MS (positive) m/z=1079.0[M+Na]⁺; $^1$H NMR (400 MHz, CDCl₃) δ=7.54-7.27 (m, 15H, ($C_6H_5$)—CH₂—), 5.60 (br.s, 1H, H-1), 5.57 (s, 1H, Ph-CH=), 4.89-4.60 (m, 8H, CCl₃—CH₂—OCO—, CH₃—CH₂—OCO—, Ph-CH₂—), 4.43-4.39 (m, 1H, H-6'''), 4.31-4.39 (m, 4H, Ph-CH₂—, H-1', Lac-αH), 3.95-3.91 (m, 1H, H-3), 3.82-3.63 (m, 6H, H-2, H-4, H-6, H-4', H-6'), 3.43-3.41 (m, 2H, H-2', H-5), 3.22-3.21 (m, 2H, H-3', H-5'), 1.35-1.27 (m, 6H, Lac-Me, CH₃—CH₂—OCO). Found: C, 51.68; H, 5.33; N, 2.35. Calcd for $C_{44}H_{50}Cl_6N_2O_{15}$: C, 51.24; H, 5.12; N, 2.54%.

(3) Preparation of 4'-O-disaccharide (Compound 13)

The compound 4 (1.5 g, 1.36 mmol) was dissolved in anhydrous CH₃CN (13 mL) to obtain a triethylamine borane (150 mg, 2.05 mmol) solution. Then, borane trifluoride diethyl etherate (960 mg, 6.80 mmol) was dropwise added to the triethylamine borane solution at 0° C. The reaction mixture was stirred at room temperature for 30 minutes, quenched with ice-cooled saturated NaHCO₃ (100 mL), and extracted with EtOAc (100 mL×2). The organic layer was washed with a 10% citrate solution (15 mL×4), a saturated NaHCO₃ solution (150 mL), and brine (100 mL), dried over Na₂SO₄, and concentrated in vacuo. The residue was purified by silica gel chromatography (180 g, toluene:EtOAc=4:1) to give the titled compound (1.13 g, 73%) as a colorless solid:

$[\alpha]_D^{23}$=+25.6 (c 1.00, CHCl₃); ESI-TOF-MS (positive) m/z=1121.6 [M+Na]; $^1$H NMR (400 MHz, CDCl₃) δ=7.43-7.27 (15H, m, ($C_6H_5$)—CH₂—), 5.85-5.79 (1H, m, —CH₂—CH=CH₂), 5.26-5.13 (3H, m, —CH₂—CH=CH₂, H-1), 4.86-4.50 (9H, m, CCl₃—CH₂—OCO—, CH₃—CH₂—OCO—, Ph-CH₂—), 4.33-4.04 (5H, m, Ph-CH₂—, Lac-αH, —CH₂—CH=CH₂), 3.97-3.57 (10H, m, —CH₂—CH=CH₂, H-3, H-4, H-6, H-3', H-4', H-6'), 3.46-3.36 (2H, m, H-2', H-5), 3.27-3.23 (1H, m, H-5'), 1.29-1.20 (6H, m, Lac-CH₃, CH₃—CH₂—OCO). Found: C, 51.68; H, 5.33; N, 2.35. Calcd for $C_{47}H_{56}Cl_6N_2O_{15}$: C, 51.24; H, 5.12; N, 2.54%.

(4) Preparation of Fully Protected Tetrasaccharide (Compound 14)

TMSOTf (18 μl, 0.15 mmol) was added to a mixture of the compound 12 (2.7 g, 38 mmol), the compound 13 (1.65 g, 30 mmol), and MS4A in anhydrous dichloromethane (75 mL) at −15° C., and the reaction mixture was stirred at −15° C. for 10 minutes. The reaction solution was quenched with an ice-cooled saturated NaHCO₃ solution (100 mL), and extracted with CHCl₃ (100 mL). The organic layer was washed with NaHCO₃ (60 mL×2) and brine (60 mL), dried over Na₂SO₄, and concentrated in vacuo. The residue was purified by silica gel chromatography (300 g, toluene:EtOAc=10:1) to give the titled compound (2.33 g, 79%) as a pale yellow solid:

$[\alpha]_D^{23}$=−1.7 (c 1:00, CHCl₃); ESI-TOF-MS (positive) m/z=2159.0 [M+Na]⁺; $^1$H NMR (400 MHz, CDCl₃) δ=7.51-7.27 (30H, m, ($C_6H_5$)—CH₂—), 5.86-5.76 (1H, m, —CH₂—CH=CH₂), 5.56 (1H, s, Ph-CH=), 5.25-4.98 (4H, m, —CH₂—CH=CH₂, Ph-CH₂—, H-1), 4.88-4.33 (17H, m, CCl₃—CH₂—OCO—, CH₃—CH₂—OCO—, Ph-CH₂—), 4.32-3.90 (12H, m, Ph-CH₂—, Lac-αH, H-1'', H-1', H-1''', H-6m, —CH₂—CH=CH₂), 3.87-3.01 (24H, m, Ph-CH₂—, H-2, H-3, H-4, H-5, H-6, H-2', H-3', H-4', H-6', H-2'', H-3'', H-4'', H-5'', H-6'', H-2''', H-3''', H-4''', H-5'', H-6'''), 1.32-1.27 (12H, m, Lac-CH₃, CH₃—CH₂—OCO).

(5) Preparation of 2-N-acetyl-tetrasaccharide (Compound 21)

Zn—Cu (made from 1 g Zn) was added to a solution of the compound 14 (1.05 g, 0.46 mmol) in acetic acid, and the reaction mixture was stirred at room temperature for one hour. Insoluble materials were removed by filtration, and the filtrate was concentrated under vacuum. The residual solvent was removed by co-evaporation with toluene (5 mL×3). The crude product was dissolved in pyridine (7 mL) and acetic anhydride (7 mL). The reaction mixture was stirred at room temperature for 30 minutes and concentrated in vacuo. The residual solvent was removed by co-evaporation with toluene (5 mL×3). The residue was purified by silica gel chromatography (80 g, CH₃Cl:acetone=3:1) to give the titled compound (750 mg, quant.) as a white solid:

[α]$_D^{23}$=−7.4 (c 1.00, CH$_3$Cl); ESI-TOF-MS (positive) m/z=1609.2[M+H$^+$], 1631.6[M+Na]$^+$.

(6) Preparation of Tetrasaccharide (Compound 23) with Free Carboxylic Acid

LiOH (28 mg, 0.66 mmol) was added to a solution of the compound 21 (180 mg, 0.11 mmol) in dioxane:THF:H$_2$O (2:4:1, 1.2 mL), and the reaction mixture was stirred at room temperature for one hour. The reaction solution was neutralized with Dowex H$^+$ (Dowex 50W-x8 200-400 mesh H form, Dow Chemical) and applied to a HP-20 column (2 cm×40 cm). Organic and inorganic salts were removed by elution with H$_2$O (300 mL), and the titled compound (170 mg, quant.) as a white solid was recovered by elution with methanol.

ESI-TOF-MS (positive) m/z=1575.1[M+Na]$^+$ (7) Preparation of Protected Tetrasaccharide Dipeptide (Compound 25)

WSCI.HCl (37 mg, 0.25 mmol) and triethylamine (48 μl, 0.47 mmol) were added to a solution of the compound 23 (122 mg, 0.078 mmol) and HOBt (33.5 mg, 0.25 mmol) in dichloromethane (14 mL) at 0° C. The reaction mixture was stirred at room temperature overnight, diluted with EtOAc, and filtered to remove insoluble materials. The filtrate was concentrated and dissolved in CHCl$_3$. The resultant CHCl$_3$ solution was washed with citric acid (1M, 20 mL), H$_2$O (20 mL), saturated NaHCO$_3$ (20 mL), and brine (20 mL). The organic layer was dried over Na$_2$SO$_4$, and concentrated in vacuo. The residue was purified by silica gel chromatography (20 g, CHCl$_3$:methanol=20:1) to give the titled compound (143 mg, 86%) as a white solid:

ESI-TOF-MS (positive) m/z=2153.52[M+Na]$^+$; $^1$H NMR (400 MHz, CDCl$_3$) δ=7.52-7.15 (40H, m), 5.58 (1H, m), 5.57 (1H, s), 5.56-5.07 (6H, m), 4.86 (1H, d, J=12.3 Hz), 4.83 (1H, d, J=3.7 Hz), 4.74 (1H. dd, J=12.1 Hz), 4.66-4.57 (4H, m), 4.35-4.24 (8H, m), 4.09-3.92 (6H, m), 3.83-3.59 (12H, m), 3.53-3.43 (10H, m), 3.39-3.35 (1H, m), 3.34-3.20 (1H, m), 2.56-2.41 (4H, m), 2.17-2.03 (7H, m), 1.93 (3H, s), 1.88 (3H, s), 1.73 (3H, s), 1.57-1.53 (3H, m), 1.43 (1H, d, J=6.9 Hz), 1.37-1.33 (3H, m), 1.26 (1H, m). Found: C, 62.03; H, 6.63; N, 6.38. Calcd for C$_{113}$H$_{138}$N$_{10}$O$_{31}$.3H$_2$O: C, 62.08; H, 6.64; N, 6.41%.

(8) Preparation of Tetrapeptide (Compound 27)

The titled compound was prepared in a similar manner to the preparation of the compound 25: ESI-TOF-MS (positive) m/z=1400.53-[(M+2H)$^{2+}$].

(9) Preparation of Tetrasaccharide Dipeptide (Compound 32, as Represented by Formula 1)

A solution of the compound 25 (300 mg, 0.071 mmol) in anhydrous THF (6 mL) was degassed, and a solution of H$_2$-activated [Ir(cod)(MePh$_2$P)$_2$]PF$_6$ (23 mg, 0.027 mmol) in anhydrous THF (3 mL) was added thereto. The reaction mixture was stirred at room temperature under a nitrogen atmosphere for one hour, and a solution of H$_2$-activated [Ir(cod)(MePh$_2$P)$_2$]PF$_6$ (23 mg, 0.027 mmol) in anhydrous THF (3 mL) was added thereto. The reaction mixture was stirred at room temperature under a nitrogen atmosphere for one hour, and iodine (35 mg, 0.142 mmol) and water (0.5 mL) were added thereto. The reaction mixture was stirred for further 10 minutes, quenched with aqueous Na$_2$SO$_3$ (5%, 100 mL), and extracted with EtOAc (50 mL). The organic layer was washed with aqueous Na$_2$S$_2$O$_2$ (5%, 10 mL×2), a saturated NaHCO$_3$ solution (100 mL×2), and brine (50 mL), dried over Na$_2$SO$_4$, and concentrated in vacuo. The residue was purified by silica gel chromatography (20 g, toluene:EtOAc=5:1) to give 1-liberated tetrasaccharide (260 mg, 88%) as a pale yellow solid: ESI-TOF-MS (positive) m/z=2113.6[M+Na]$^+$.

Palladium hydroxide (100 mg) on carbon in acetic acid was added to a solution of 1-liberated tetrasaccharide (86 mg, 0.04 mmol) in acetic acid (3 mL), and the reaction mixture was stirred under H$_2$ (20 atm) for one day. The palladium catalyst was removed by filtration, and the filtrate was concentrated and lyophilized from H$_2$O to give the titled compound (39 mg, 70%) as a white solid:

ESI-TOF-MS (positive) m/z=685.3 [M−2H]$^{2-}$; HRMS-ESI FT-ICR(negative): (M) calcd for C$_{54}$H$_{88}$N$_{10}$O$_{31}$, 1372.561; found, 1372.555; $^1$H NMR ((600 MHz, D$_2$O): δ=5.16-5.15 (d, J=3.0 Hz, 1H, H-1), 4.46-4.42 (m, 3H), 4.36-4.32 (m, 2H), 4.30-4.27 (m, 2H, iGln-CH), 4.26-4.19 (m, 2H), 3.86-3.30 (m, 24H), 2.31 (m, 4H, iGln-γ-CH$_2$), 2.12-2.03 (m, 4H, iGln-β-CH$_2$), 1.96-1.95 (s, 12H, NHC(O)CH$_3$ X 4), 1.37-1.35 (m, 6H, Ala-β-CH$_3$), 1.31-1.28 (m, 6H, Lac-β-CH$_3$).

(10) Preparation of Tetrasaccharide Tripeptide (Compound 33, as Represented by Formula 2)

A solution of palladium hydroxide (100 mg) in acetic acid was added to a solution of the compound 27 (95 mg, 0.036 mmol) in acetic acid (3 mL), and the reaction mixture was stirred under H$_2$ (20 atm) for one day. Progress of the reaction was monitored by thin-layer chromatography (TLC) analysis, and the hydrogenolysis was continued until deprotection was terminated. The palladium catalyst was removed by filtration through a cerite pad, and the filtrate was concentrated. The residue was lyophilized from acetonitrile-H$_2$O to give the titled compound (39 mg, 50%) as a white powder:

ESI-TOF-MS (negative) m/z=834.5 [M-2H]$^{2"}$; HRMS-ESI FT-ICR (negative): (M) calcd for C$_{69}$H$_{118}$N$_{14}$O$_{33}$, 1670.798; found, 1670.817; $^1$H NMR (500 MHz, D$_2$O): δ=4.86-4.80 (m, 1H, H-1) 4.46-4.40 (m, 3H), 4.36-4.05 (m, 8H, Lac-α-CH, Ala-α-CH, iGln-α-CH, Lys-α-CH), 3.86-3.30 (m, 26H), 3.00-2.90 (t, J=11.4, 4H, Lys-ε-CH$_2$), 2.37-2.31 (t, J=9.5, 4H, iGln-γ-CH$_2$), 2.09-2.0 (m, 4H, iGln-β-CH$_2$), 2.02-1.81 (m, 18H, NHC(O)CH$_3$ X 4, Lys-β-CH X 2, Lys-δ-CH X 2), 1.78-1.69 (m, 2H, Lys-δ-CH X 2), 1.58-1.70 (m, 4H, Lys-γ-CH$_2$ X 2), 1.61-1.4 (m, 2H, Propyl CH$_3$—CH$_2$), 1.40-1.35 (m, 6H, Ala-β-CH$_3$), 1.31-1.28 (m, 6H, Lac-β-CH$_3$), 0.85-0.80 (t, J=9.3, 3H, Propyl CH$_3$).

(11) Preparation of Tetrasaccharide Tetrapeptide (Compound 35, as Represented by Formula 3)

The titled compound was prepared in a similar manner to the preparation of the compound 33 from the compound 27:

ESI-TOF-MS (negative) m/z=905.1 [M−2H]$^{2-}$; HRMS-ESI FT-ICR (negative): (M) calcd for C$_{75}$H$_{128}$N$_{16}$O$_{35}$, 1812.873; found, 1812.896; $^1$H NMR (500 MHz, D$_2$O): δ=4.86-4.80 (m, 1H, H-1), 4.46-4.40 (m, 3H), 4.36-3.95 (m, 10H, Lac-α-CH, Ala-α-CH, D-iGln-α-CH, Lys-α-CH), 3.86-3.30 (m, 26H), 3.00-2.90 (t, J=7.5, 4H, Lys-ε-CH$_2$), 2.40-2.31 (t, 4H, iGln-γ-CH$_2$), 2.09-1.82 (m, 22H, iGln-β-CH$_2$ X 2, NHC(O)CH$_3$ X 4, Lys-β-CH$_2$ X 2, Lys-δ-CH X 2), 1.78-1.4 (m, 8H, Lys-δ-CH X 2, Lys-γ-CH$_2$ X 2, Propyl CH$_3$—CH$_2$), 1.40-1.22 (m, 12H, Ala-β-CH$_3$ X 4, Lac-β-CH$_3$ X 2), 0.85-0.80 (m, 3H, Propyl CH$_3$).

(12) Preparation of Tetrasaccharide Pentapeptide (Compound 37, as Represented by Formula 4)

The titled compound was prepared in a similar manner to the preparation of the compound 33 from the compound 27:

ESI-TOF-MS (negative) m/z=976.64 [M−2H]$^{2-}$; HRM-SESI FT-ICR (negative): (M) calcd for C$_{81}$H$_{138}$N$_{18}$O$_{37}$, 1954.947; found, 1954.939; $^1$H NMR (500 MHz, D$_2$O): δ=4.86-4.80 (m, 1H, H-1), 4.46-4.40 (m, 3H), 4.36-4.0 (m, 12H, Lac-α-CH, Ala-α-CH, iGln-α-CH, Lys-α-CH), 3.86-3.30 (m, 26H), 2.95-2.91 (t, J=7.5, 4H, Lys-ε-CH$_2$), 2.40-2.31 (t, J=7.0, 4H, iGln-γ-CH$_2$), 2.09-1.82 (m, 22H, iGln-β-CH$_2$ X 2, NHC(O)CH$_3$ X 4, Lys-β-CH$_2$ X 2, Lys-δ-CH X 2), 1.78-1.4

(m, 8H, Lys-6-CH X 2, Lys-γ-CH$_2$ X 2, Propyl CH$_3$—CH$_2$), 1.40-1.22 (m, 12H, Ala-β-CH$_3$ X 6, Lac-β-CH$_3$ X 2), 0.85-0.80 (m, 3H, Propyl CH$_3$).

Example 4

Evaluation of Effect of Natural or Synthetic PGN on PO Activation

In this Example, an effect of natural or synthetic PGN on the activation of PO in the hemolymph of *Tenebrio molitor* larvae was evaluated.

Figure 2:
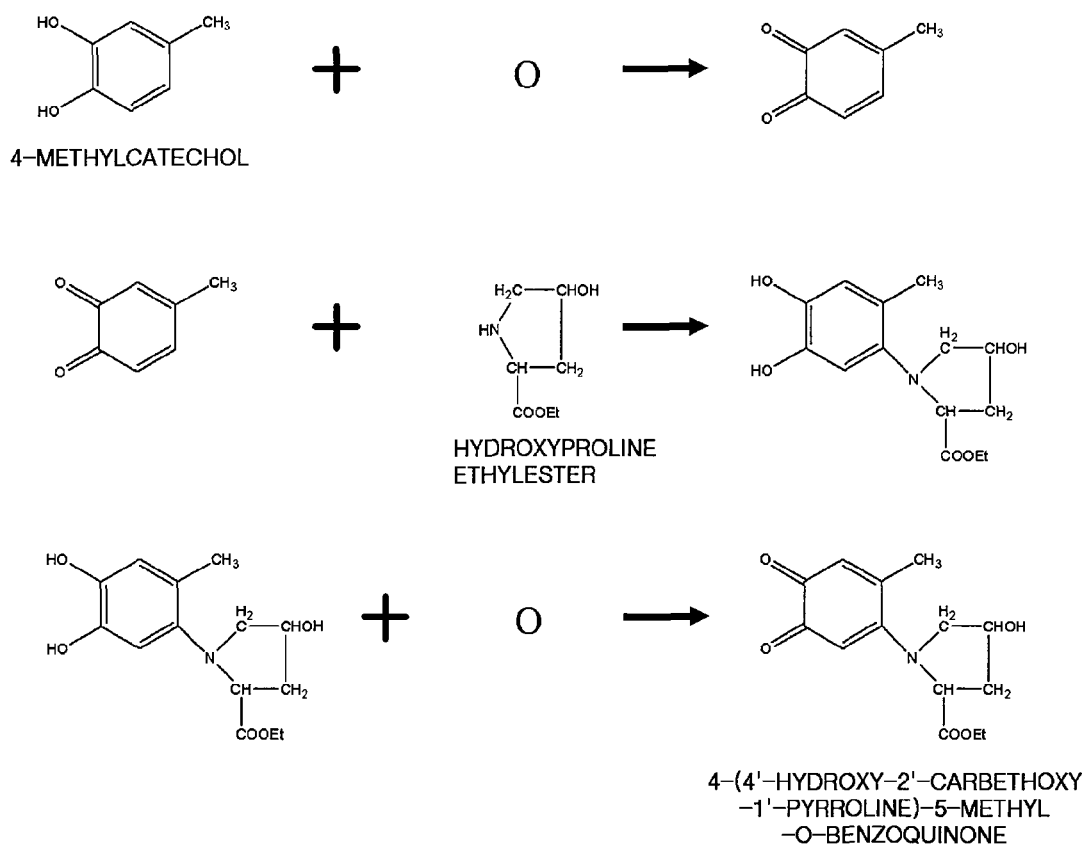
FIG. 2 illustrates a principle of a Pye-spectrophotometric assay for measuring PO activity.

PO activity was assayed according to a Pye-spectrophotometric method using a substrate solution (4-methylcatechol, and 4-hydroxyproline ethylester in HCl). 4-methylcatechol was oxidized to quinone by PO, which was then converted through a non-enzymatic reaction with 4-hydroxyproline ethylester in HCl to 4-(4'-hydroxyl-2'-carbethoxy-1'-pyrroline)-5-methyl-o-benzoquinone, a stable compound having maximum absorbance at 520 nm (see FIG. 2)

Each of 10 μl (1 μg) of a 10% β-1,3-glucan solution, 10 μl. (1 μg) of a 10% *S. aureus* PGN solution, 10 μl (10 ng) of a 10% *M. luteus* PGN solution, and 10 μl (1 μg) of a 10% synthetic PGN (for each of the compounds of Formulae 1-4) solution was incubated together with 30 μl (protein 350 μg) of the hemolymph of *Tenebrio molitor* larvae at 30° C. for 5 minutes. Then, 4 μl of 4-methylcatechol (250 mM), 16 μl of 4-hydroxyproline ethylester (62.5 mM) in HCl, and 5 μl of 1M CaCl$_2$ (10 mM) were added thereto. Then, 20 mM Tris-HCl (pH 8.0) was added to a final volume of 500 μl. The reaction mixture was incubated at 30° C. and the absorbance of the reaction solution was measured at 520 nm (see FIG. 3).

Figure 3:
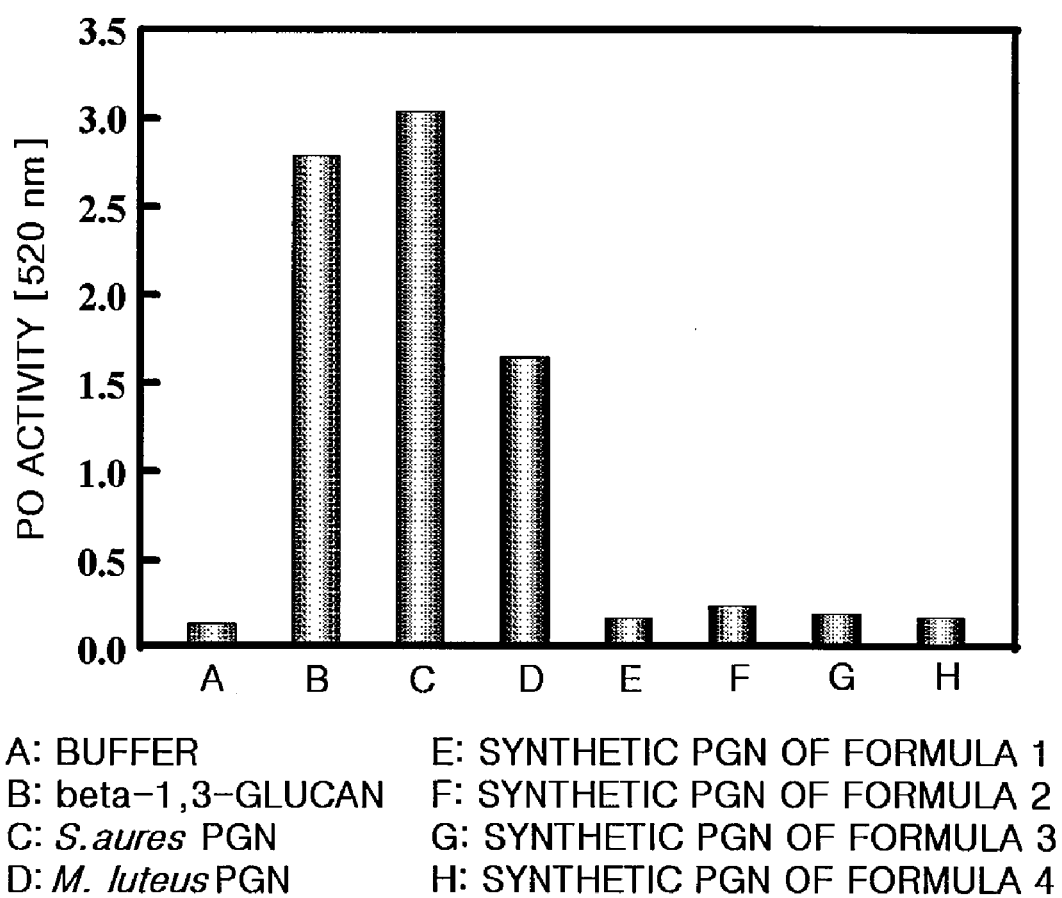
FIG. 3 is a graph illustrating the effects of natural peptidoglycan (PGN), beta-1,3-glucan, and synthetic PGN on PO activity.

It was found that the β-1,3-glucan, the *S. aureus* PGN solution, and the *M. luteus* PGN solution activated the PGN-dependent pro-PO cascade in the hemolymph of *Tenebrio molitor* larvae, whereas the synthetic PGN having a relatively simple structure did not activate the PGN-dependent pro-PO cascade (see FIG. 3).

Figure 4:
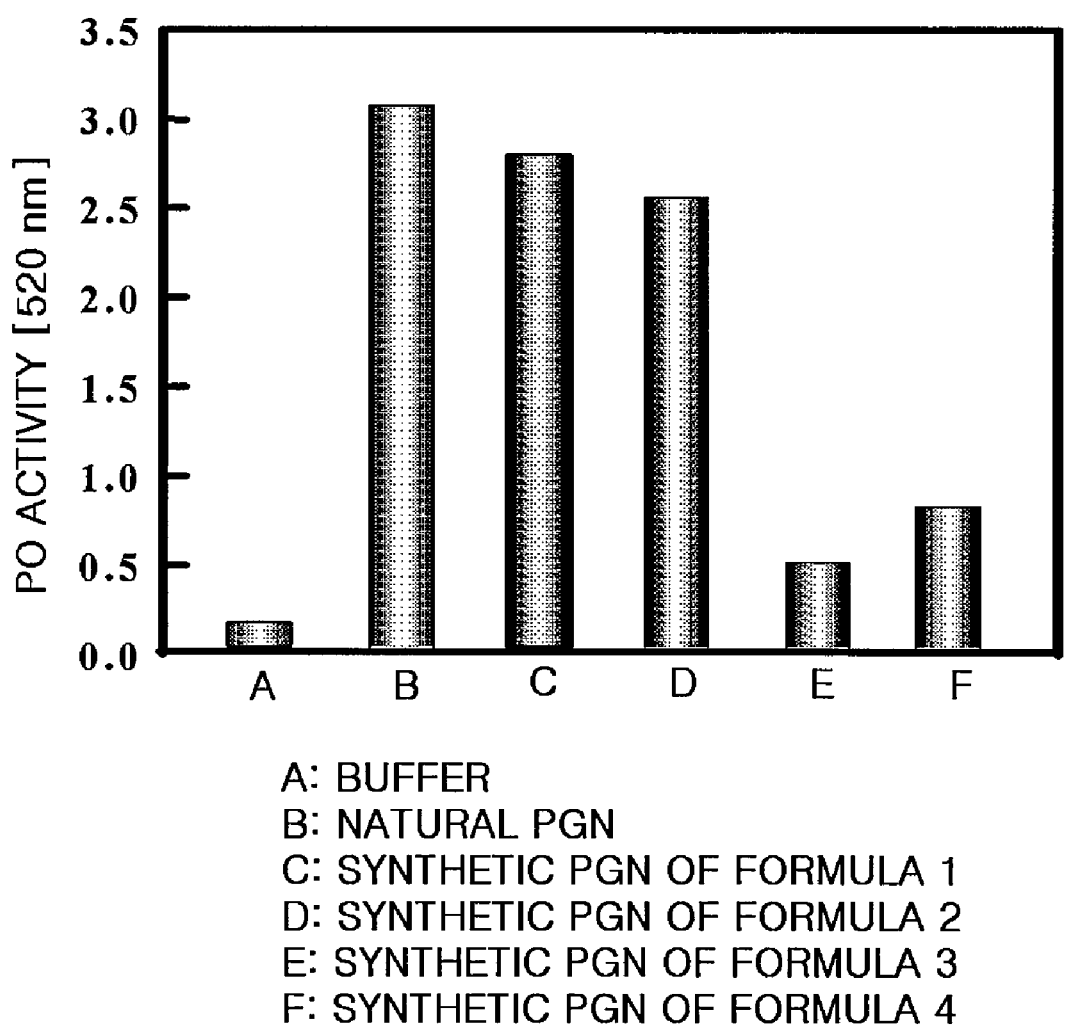
FIG. 4 is a graph illustrating the degree of inhibition of natural PGN-dependent PO activity by synthetic PGN.

Meanwhile, PO activity was also measured in the presence of 1 μg of *S. aureus* PGN and 1 μg of each of the synthetic PGNs. It was found that the synthetic PGNs inhibited PGN-dependent PO activity even though the degree of inhibition of PGN activity was different by synthetic PGN (see FIG. 4). In particular, the compound 35 of Formula 3, where four amino acids were linked to N-acetylmuramic acid, functioned as the strongest competitive inhibitor of natural PGN-dependent PO activity. These results reveal that the synthetic PGN of Formula 3 is optimally recognized by PGN-recognition proteins in the hemolymph of *Tenebrio molitor* larvae.

Figure 5:
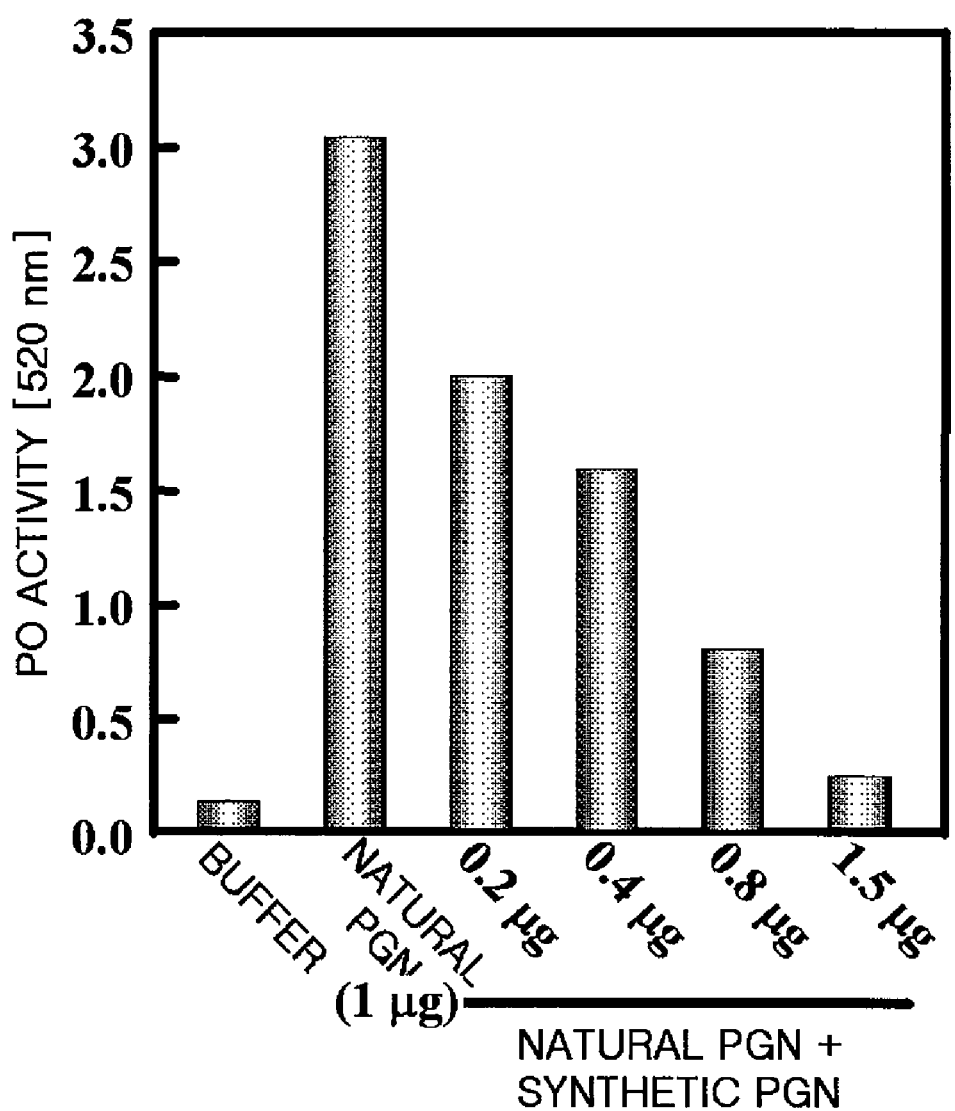
FIGS. 5 and 6 are graphs illustrating the degree of inhibition of natural PGN-dependent PO activity and amidase activity, respectively, with respect to the concentration of synthetic PGN.

Furthermore, PO activity was also measured in the presence of 1 μg of *S. aureus* PGN with an incremental addition of the synthetic PGN of Formula 3 (0.2, 0.4, 0.8, and 1.5 μg). It was found that PO activity was inhibited in a synthetic PGN concentration-dependent manner (see FIG. 5).

Example 5

Evaluation of Effect of Natural or Synthetic PGN on Amidase Activity

10 μl of a 10% gram-positive *S. aureus* PGN (final concentration: 1 μg) solution and 10 μl of a 10% synthetic PGN (the compound 35 of Formula 3) solution were incubated in the presence of 40 μM trypsin MCA (t-butyloxycarbonyl-benzyl-L-phenylalanyl-L-seryl-L-arginine-4-methylcoumaryl-7-amide; Boc-Phe-Ser-Arg-MCA) as a substrate at 30° C., and fluorescence was measured at 380 nm (excitation wavelength) and 460 nm (emission wavelength) using a fluorescence spectrophotometer (model UV-160A, Shimadzu).

Figure 6:
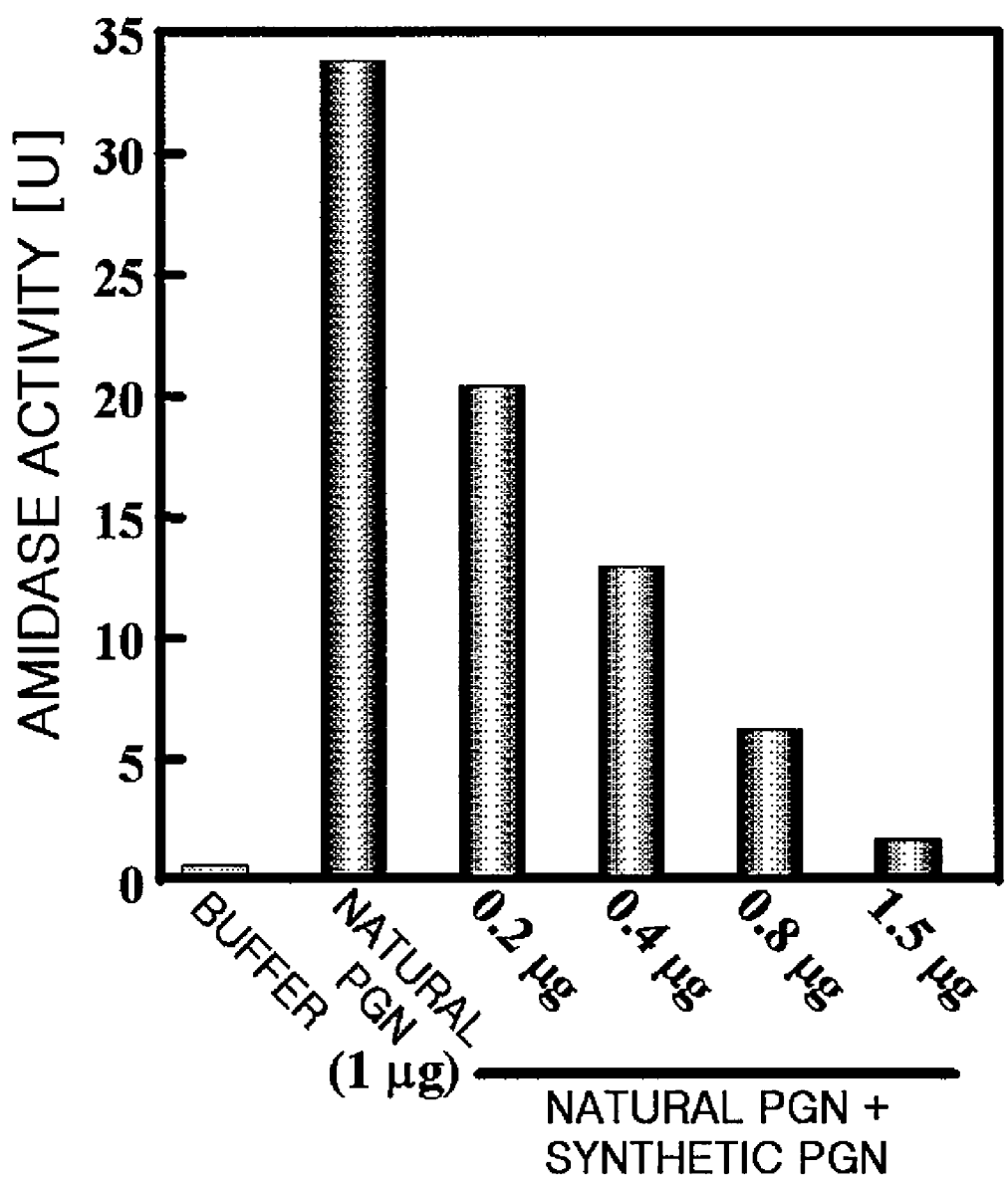

As a result, it was found that the amidase activity exhibited the same inhibition pattern as the PO activity (see FIG. 6). This result reveals that synthetic PGN is only involved in the PGN recognition.

Example 6

Purification of PGN-Recognition Protein from *Tenebrio molitor* Larvae (1) Preparation of Synthetic PGN-Coupled Column First, a CNBr Sepharose 4B resin was activated with 1 mM HCl. Then, a solution of 20 mg of the synthetic PGN of Formula 3 in a binding buffer (0.1 M NaHCO$_3$, 0.5 M NaCl) (pH 8.3) was applied to the CNBr Sepharose 4B resin. The resultant mixture was incubated at room temperature for one hour, stirred with a blocking buffer (0.1 M Tris solution, pH 8.0) at room temperature for two hours, and washed with a 0.1 M acetate buffer (pH 4.0, 0.5 M NaCl, ×3) and a 0.1 M Tris-HCl buffer (pH 8.0, 0.5 M NaCl, ×3) to prepare a PGN-coupled Sepharose 4B resin.

In order to determine if the synthetic PGN was coupled to the CNBr Sepharose 4B resin, absorbance measurements at 218 nm were performed for the solution of the synthetic PGN in the binding buffer and the solution obtained after incubating the solution of the synthetic PGN in the binding buffer and the CNBr Sepharose 4B resin, and an absorbance reduction (%) was calculated. As a result, the coupling reaction between the synthetic PGN and the CNBr Sepharose 4B resin led to the production of PGN-coupled resin with an 89% yield, thereby to make a PGN (32 ml)-coupled column.

Meanwhile, a control column was made in the same manner as described above except that no synthetic PGN was used.

(2) Separation and Purification of 20 kDa PGN-Recognition Protein (a) Purification with Synthetic PGN-Coupled Column A 0.5 M DFP solution was added to 160 ml of the hemolymph of *Tenebrio molitor* larvae extracted with an anticoagulation buffer (pH 5.0) to a final concentration of 2 mM. The reaction mixture was incubated at 4° C. for two hours, and dialyzed with a 3 mM EDTA-containing 50 mM Tris buffer (pH 6.0) at 5° C. for 12 hours.

An open column (ψ3 cm×25 cm) was packed with about 30 ml of the PGN-coupled Sepharose resin, and about 160 ml of the dialyzed solution of the hemolymph of *Tenebrio molitor* larvae was loaded on the PGN-coupled column at a flow rate of 0.6 ml/min.

The PGN-coupled column was washed with a 3 mM EDTA-containing 50 mM Tris buffer (pH 6.0) at a flow rate of 0.6 ml/min, and proteins were eluted from the PGN-coupled column using a 3 mM EDTA- and 1 M NaCl-containing 50 mM Tris buffer (pH 6.0) at a flow rate of 0.4 ml/min until no protein was detected through absorbance measurement at 280 nm. The concentration of the proteins in the eluted solution was determined through absorbance measurement at 280 nm, and the purity and content of the proteins were analyzed by SDS-PAGE.

A pass-through solution and a 1M NaCl-eluted solution were obtained from the PGN-coupled column, and concentrated using an ultrafiltration kit (Amicon) equipped with a membrane having a molecular cut-off size of 10,000.

Figure 7:
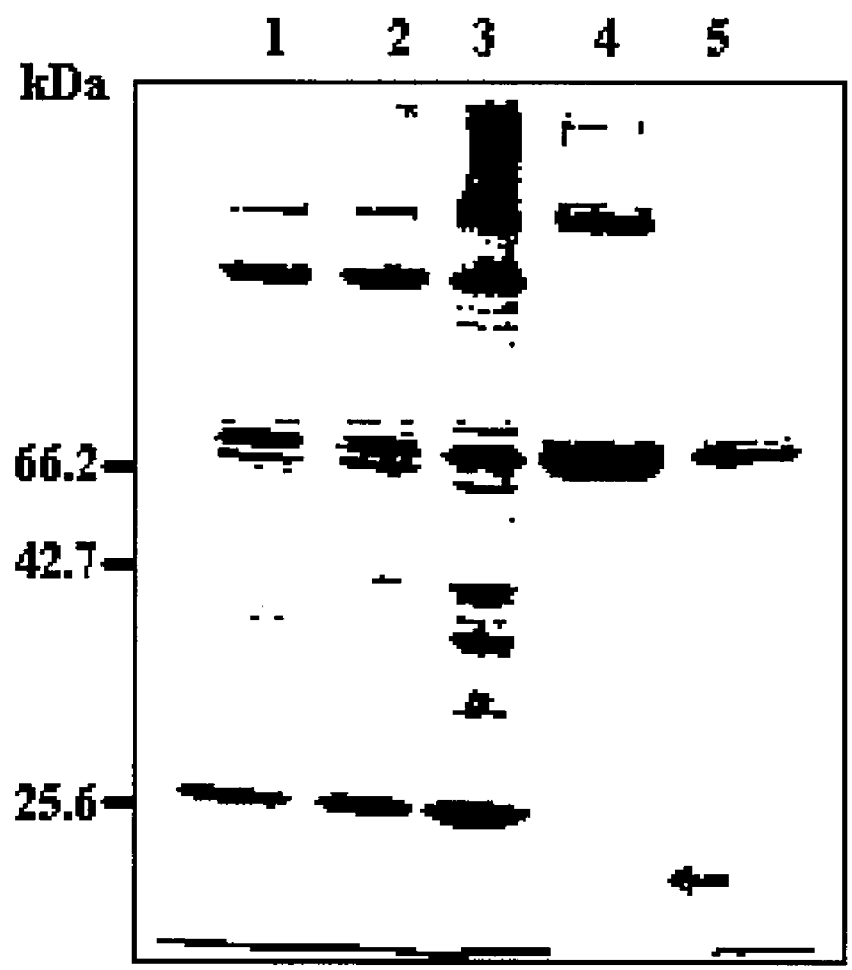
FIG. 7 shows the results of Sodium Dodecyl Sulfate-Poly-Acrylamide Gel Electrophoresis (SDS-PAGE) performed using the hemolymph of *Tenebrio molitor* larvae before and after dialysis, and solutions eluted from a synthetic PGN-coupled column and a control column.

The hemolymph of *Tenebrio molitor* larvae before the dialysis (lane 1 of FIG. 7) and after the dialysis (lane 2 of FIG. 7), the pass-through solution from the PGN-coupled column (lane 3 of FIG. 7), the 1M NaCl-eluted solution from the PGN-coupled column (lane 4 of FIG. 7), and a 1M NaCl-eluted solution from the control column (lane 5 of FIG. 7) were analyzed by SDS-PAGE. About 25 μg of protein was loaded on a SDS-PAGE gel.

The gel patterns of proteins in the 1M NaCl-eluted solutions from the control column and the PGN-coupled column were compared and analyzed. The SDS-PAGE results showed that an about 20 kDa protein was specifically present only in the eluted solution from the PGN-coupled column (see FIG. 7).

(b) Purification with Toyopearl HW55S FPLC Column

The 1M NaCl-eluted solution from the PGN-coupled column in (a) was concentrated using an ultrafiltration kit (Amicon) equipped with a membrane having a molecular cut-off size of 10,000 to prepare a concentrate sample.

A FPLC column ($\psi$1.0 cm×30 cm) was packed with Toyopearl HW55S resin and equilibrated with a 3 mM EDTA- and 0.15 M NaCl-containing 50 mM Tris solution (pH 6.0) at a flow rate of 0.2 ml/min.

The concentrate sample was loaded on the Toyopearl HW55S FPLC column and fractionated by peaks. The total fractions were collected according to the profile pattern, and analyzed by SDS-PAGE to identify the pattern of protein bands.

Figures 8, 9:
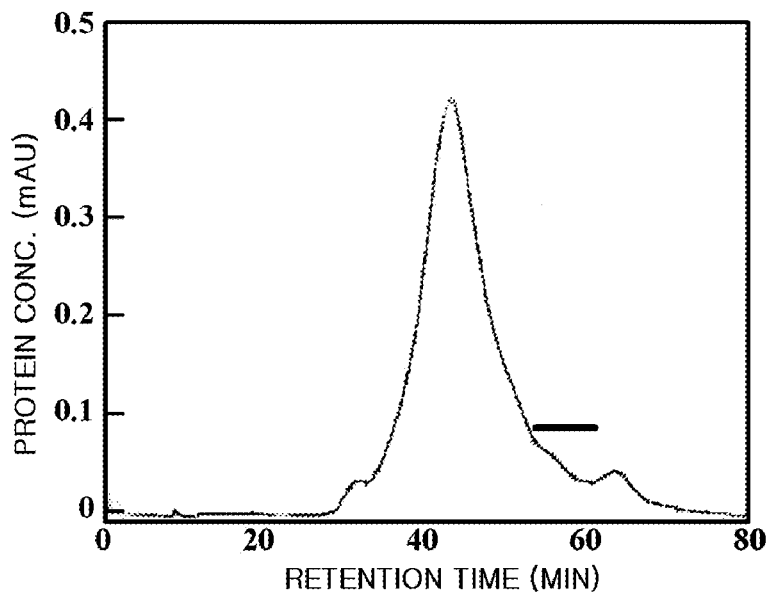
FIG. 8 shows amino acid sequences of the N-terminal region (A) and three fragments (B) of a 20 kDa protein eluted from a synthetic PGN-coupled column, determined using Edman degradation.
FIG. 9 is a graph illustrating an elution profile of a PGN-recognition protein of *Tenebrio molitor* larvae by Toyopearl HW55S column chromatography.

The SDS-PAGE results showed that the fractions were further purified *Tenebrio molitor* larval PGN-recognition protein (i.e., transmembrane PGN-recognition protein (Tm-PGRP)) fractions with about 80% of other proteins removed, than the fractions of (a). The SDS-PAGE results also showed that elution of the *Tenebrio molitor* larval PGN-recognition protein from the column started about 55 minutes after the loading (see FIG. 9). The further purified *Tenebrio molitor* larval PGN-recognition protein fractions were used for the subsequent experiments.

(c) Purification with Hydroxyapatite Column

A FPLC column ($\psi$0.5 cm×10 cm) was packed with a hydroxyapatite resin exhibiting differential separation efficiency according to the ionic strength of a phosphate group, and the protein fractions obtained from the Toyopearl HW55S column were loaded on the hydroxyapatite column. At this time, a 10 mM sodium phosphate buffer (pH 6.5) was used as a buffer A, and a 300 mM sodium phosphate buffer (pH 6.5) was used as a buffer B. The buffer A and the buffer B were allowed to flow at a to rate of 0.4 id/min according to the concentration gradient of phosphate (75 mM at maximum at 120 minutes). Fractions showing PGN-dependent PO activity were collected and purified as follows.

Figure 10:
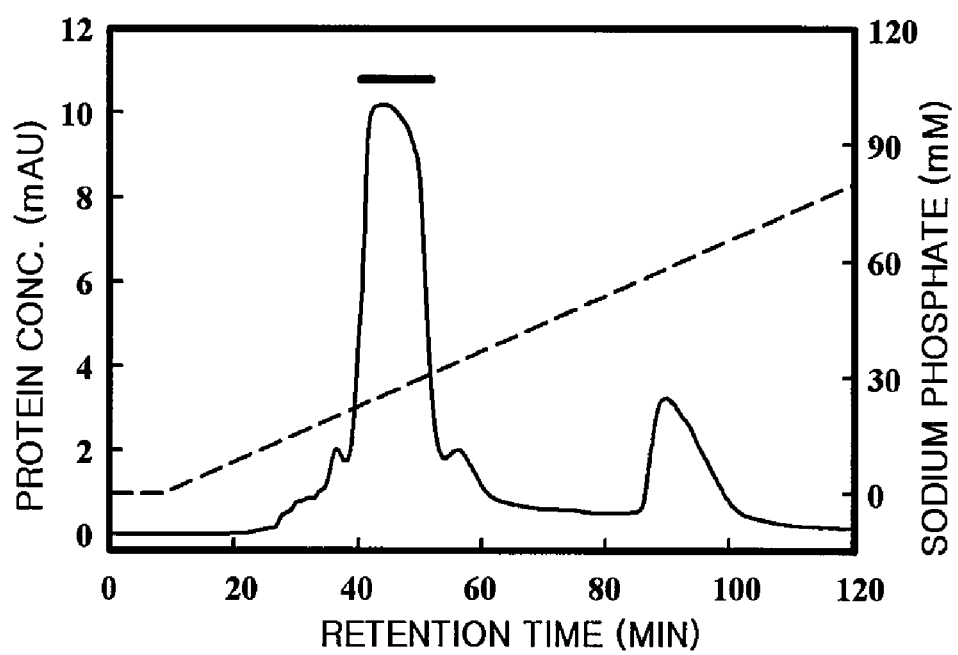
FIG. 10 is a graph illustrating an elution profile of a PGN-recognition protein of *Tenebrio molitor* larvae by hydroxyapatite column chromatography.

The hydroxyapatite column chromatographic results of the fractions obtained from the Toyopearl HW55S column are illustrated in FIG. 10.

The total fractions were separated and recovered according to the pattern of the elution profile, and analyzed by SDS-PAGE to identify the pattern of protein bands. Referring to FIG. 10, Tm-PGRP started to be eluted at the concentration of about 24 mM phosphate ions. Further purified Tm-PGRP fractions with about 54% of other proteins removed were obtained and used for the subsequent purification.

(d) Purification with Mono-Q FPLC column

Mono-Q FPLC column chromatography was performed using the properties of Mono-Q resin, an anionic exchange resin, to purify only PGN-recognition protein from the proteins separated from the hydroxyapatite column. The Mono-Q FPLC column chromatography was performed using buffer A (50 mM Tris buffer (pH 6.5)) and buffer B (buffer A+1 M NaCl) according to the concentration gradient of the buffer A and the buffer B. The content of the buffer B was gradually increased as follows: 0% for initial 5 minutes, 30% for 30 minutes, and 100% for 45 minutes. The concentration of protein in the eluted fractions was measured by measuring UV absorbance at 280 nm, and the purity and content of the protein were analyzed by SDS-PAGE.

Figure 11:
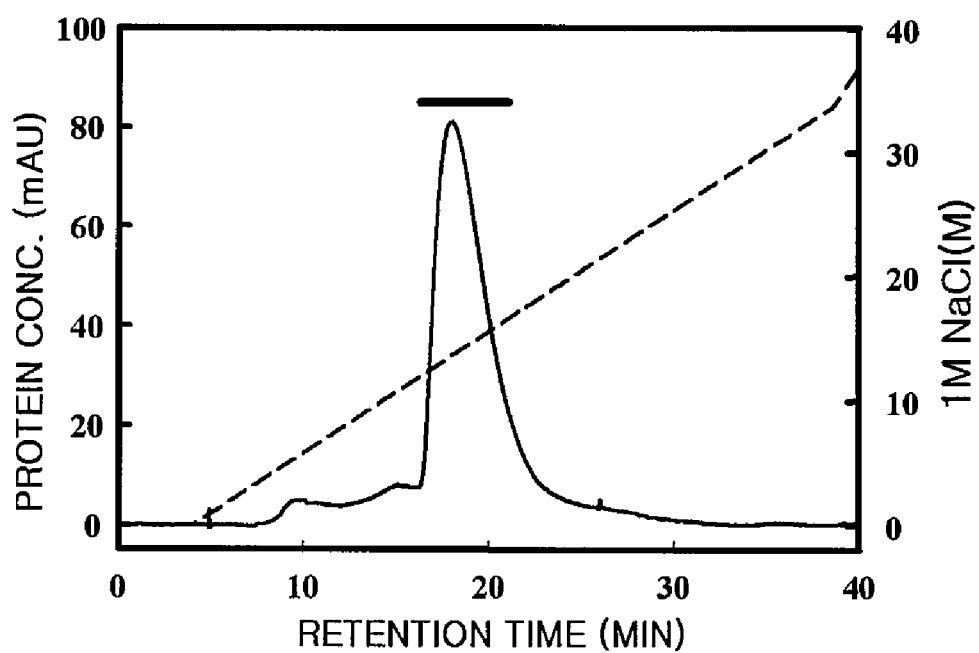
FIG. 11 is a graph illustrating an elution profile of a PGN-recognition protein of *Tenebrio molitor* larvae by Mono-Q-FPLC column chromatography.

The Mono-Q FPLC column chromatographic elution profile for the protein fractions obtained from the hydroxyapatite column is illustrated in FIG. 11. All of the fractions were separated and recovered according to the pattern of the elution profile, and analyzed by SDS-PAGE to determine the pattern of protein bands. Referring to FIG. 11, Tm-PGRP started to be eluted at about 120 mM NaCl.

Example 7

Determination of Amino Acid Sequences of N-Terminal Region and Three Fragments of 20 kDa PGN-Recognition Protein The protein purified in Example 6 was subjected to 12% SDS-PAGE for N-terminal sequencing, and then, transferred to PVDF membrane by electrophoresis in a transfer buffer (CAPS 10 mM, 10% methanol) at a constant current of 300 mA for one hour.

The PVDF membrane was stained with a CBB staining solution (0.1% CBB R-250, 50% methanol), destained with a destaining solution (50% methanol, 10% acetic acid), washed with water several times, and dried under reduced pressure. The protein bands were cut and applied to an automated amino acid sequencer to perform gas-phase amino acid sequencing on the PVDF membrane.

Meanwhile, 25 μg of the protein purified in Example 6 was reduced by 45 mM DTT and alkylated by a 100 mM iodoacetamide solution, and lysyl-endopeptidase was added thereto. The reaction mixture was incubated at 37° C. for 12 hours, and peptide fragments were loaded and purified on a HPLC $C_{18}$ column. The amino acid sequences of the purified peptides were determined with an automated amino acid sequencer.

Thus, a 20 kDa protein purified by electroelution was blotted onto PVDF membrane, and the amino acid sequences of the N-terminal region (SEQ ID NO: 3, see FIG. 8A) and three fragments (SEQ ID NOS: 4-6, see FIG. 8B) of the 20 kDa protein were determined through Edman degradation.

In particular, the NCBI blast analysis showed that the 20 kDa protein had high sequence homology with short PGN-recognition proteins present in various living organisms.

Example 8 cDNA Cloning of 20 kDa PGN-Recognition Protein, and Sequencing of Polynucleotide Encoding the PGN-Recognition Protein In Example 8, the cDNA library of *Tenebrio molitor* was screened using DNA probes designed based on the partial amino acid sequence information of the 20 kDa PGN-recognition protein obtained in Example 7. The screening was divided into first screening and second screening. Both the screenings were performed through plaque hybridization using the DNA probes.

(1) Synthesis of DNA Probes

Among peptide fragments obtained by digesting the purified protein with lysyl-endopeptidase, peptide fragments whose amino acid sequences defined a relatively small number of possible nucleotide sequences were selected. Based on the selected peptide fragments, the nucleotide sequences having an appropriate melting temperature (Tm) of 55-65° C. were designed as DNA probes.

The DNA probes were purified with a Genotech purification tool. DNA probes having a nucleotide sequence of SEQ ID NO: 7 were used for cDNA cloning of 20 kDa PGN-recognition proteins.

(2) Preparation of Host Cells

5 μl of an XL-1-Blue stock solution was coated on LB/tetracycline plates and incubated at 37° C. for 12 hours. Single colonies from the LB/tetracycline plates were inoculated onto a mixture of 5 ml of LB broth, 50 μl of 20% maltose, and 50 μl of 1 M $MgSO_4$, cultured at 37° C. while shaking until $OD_{600}$ reached 0.5-1, and centrifuged at 500×g for 10 minutes. The precipitates were resuspended in 10 mM $MgSO_4$ so that $OD_{600}$ was 0.5.

(3) Replica Preparation

Replica of amplified cDNA library from *Tenebrio molitor* larvae was taken from 12 plates (5,000 plaques/plate). That is, 200 μl of XL-1-Blue ($OD_{600}$=0.5) was added to a 5,000 plaque-producing cDNA library solution, cultured at 37° C. for 15 minutes while shaking, and mixed with 3.5 in of a top agar preheated to 48° C. The resultant mixture was rapidly stirred several times and quickly coated on NZY plates. The NZY plates were incubated at 37° C. for 13 hours to thereby give replica.

The NZY plates were left standing at 4° C. for one hour to terminate the reaction. Then, colony/plaque screen membranes (NEF-978) were carefully placed on top of the NZY plates, labeled with a needle and a red oily pen, and incubated at room temperature for 5 minutes. Second membranes were carefully placed on top of the NZY plates, labeled with a black oily pen, and incubated for 15 minutes and then in air for one hour or more to completely dry the membranes. Then, the membranes were treated with alkaline (0.5 N NaOH) for two minutes, dried for 5 minutes, neutralized with 1 M Tris/HCl (pH 7.5), and dried in air. The membranes were treated again with alkaline and neutralized in the same manner as above, and left standing at room temperature for one hour or more so that the membranes were completely dried. Then, the membranes were subjected to washing for screening. That is, the membranes were submerged in a washing buffer (3×SSC/0.1% SDS) and then squeezed out with absorbent paper to completely remove SDS.

(4) Kination of DNA Probes

DNA probes for screening positive clones were labeled as follows: 21 μl of distilled water (milli-Q, autoclave), 18 μl of a 10× kinase buffer, 9 μl (600 pM) of DNA probes, 90 μl (about 0.9 mCi) of $\gamma$-$^{32}$P-dATP, and 12 μl (40 units) of T4 polynucleotide kinase (PNK) (10 units/μl) were voltexed and spun down.

The reaction mixture was incubated at 37° C. for 30 minutes and thermally treated in a 70° C. water bath for 10 minutes. 10 μl of *E. coli* tRNA (20 μg/μl) was added thereto, and the probes were purified on a Sepharose G-50 column to selectively collect radiolabeled probes.

(5) Prehybridization

30 μl, of a prehybridization solution preheated to 60° C., together with the membranes, was placed in a plastic bag, completely degassed, sealed, and incubated at 60° C. for 5 hours. The prehybridization solution was prepared by adding distilled water to a mixture of 22.5 ml of a 20×SSC solution, 30 ml of a 50×denhart's solution, and 1.5 ml of 5 mg/ml ssssDNA to a total volume of 150 ml.

(6) Hybridization

After the prehybridization was terminated, the membranes were removed from the plastic bag. A $\gamma$-$^{32}$P-ATP-labeled DNA probe solution was added to 30 ml of a hybridization solution (5 ng DNAs/ml). The reaction mixture, together with the membranes, was placed in a plastic bag, degassed, sealed, and incubated at Tm-5° C. in a constant temperature water bath for one day. The melting temperature (Tm) of the DNA probes was estimated using Itakura's rule under which the Tm of DNA is calculated with a hydrogen bond between adenine (A) and thymine (T) set as 2° C. and that between guanine (G) and cytosine (C) set as 4° C.

The hybridization solution was prepared by adding distilled water to a mixture of 30 ml of a 20×SSC solution, 30 ml of a 50×denhart's solution, and 0.75 ml of 5 mg/ml ssssDNA to a total volume of 150 ml.

After the hybridization, the membranes were removed from the plastic bag, and washed three times (5 minutes for each) with a washing solution (3×SSC/0.1% SDS), which had been preheated to 30° C., and then once or twice with the same washing solution at 55° C. for 5 minutes. Then, the membranes were attached onto 3 MM filter papers (Whatman) with radioactivity on the membranes at about 400 cpm/filter, and placed in cassettes. X-ray films were fixed on the membranes, and the cassettes were incubated at −75° C. for about 12 hours and thawed at room temperature. The X-ray films were peeled off from the membranes in a dark room and developed. The X-ray films were aligned with the membranes to mark replica on the X-ray films.

(7) Selection of Positive Clones

Autoradiographic marks of the two membranes were aligned with each other to perform an overlay assay. Positive signals commonly detected in the two membranes were selected and identified as primary positive clones. Positive plaques were rescreened on master plates stored at 4° C. to pick single positive plaques.

(8) Secondary Screening

The single positive plaques selected through the primary screening were diluted 10-fold (×3) with LB liquid media. 1 μl of the diluted solution was placed in 1 μl of a 3 μl $CHCl_3$-containing SM buffer, spread on NZY plates, and incubated at 37° C. overnight. Plates containing about 100 plaques per plate were used as master plates. The master plates were subjected to replica plating, DNA immobilization, plaque hybridization, and positive plaque selection in the same manner as in the primary screening. The putative positive clones selected through the primary screening were verified by the secondary screening.

(9) Construction of Phagemids

The titer of the positive clones of 20 kDa protein verified by the secondary screening was calculated to come up with the amount that is expected to generate 2×10$^5$ plaques. Based on the estimation, 200 μl of XL-1-Blue ($OD_{600}$=1.0), 200 μl of a solution (2×10$^5$ phages) containing the positive plaques identified by the secondary screening, and 1 μl of ExAssist helper phage were placed in 50 ml falcon tubes, and incubated at 37° C. for 15 minutes. 3 ml of a LB broth was added thereto, and the resultant suspension was cultured at 37° C. for 3 hours while shaking, heated to 70° C. for 20 minutes, and centrifuged at 1,000×g for 15 minutes. The supernatant was placed in a 15 ml falcon tube and stored at 4° C.

(10) Culturing of Phagemids

In order to purify phagemids containing the gene of the 20 kDa protein, SOLR cells with no aminicillin resistant region were transformed with phagemids containing an ampicillin resistant region and grown on LB/ampicillin plates. A detailed description thereof was as follows:

10 μl and 100 μl of phagemids diluted 1,000-folds with LB broth were respectively added to 200 μl of SOLR cells ($OD_{600}$=1.0) and cultured at 37° C. for 15 minutes while shaking. 50 μl aliquots of each culture were smeared on LB/ampicillin plates and cultured at 37° C. for 12 hours. Single colonies were picked from the plates, loaded on 50 µl falcon tubes containing 5 ml of LB broth and 10 µl of ampicillin (50 mg/ml), and cultured at 37° C. for 12 hours.

(11) Separation, Purification, and Identification of Phagemids

The cultures prepared in (10) were subjected to purification by a DNA purification kit (Miniprep kit, Quiagen) according to the manufacturer's specification to obtain phagemids containing the gene of protein of interest. In order to determine the purity of the thus-obtained phagemids, 0.5 µg of phagemid DNAs, 0.5 µl (7.5 U) of EcoRI, 0.5 µl (6 U) of XhoI, and 1 µl of a 10×H buffer were mixed, and tertiary distilled water was added to the mixture to a total volume of 10 µl. The reaction mixture was incubated at 37° C. for one hour and mixed with 3 µl of a 6× loading buffer. 10 µl aliquots of the resultant solution were analyzed by 1.5% agarose gel electrophoresis. The gels were submerged in an ethidium bromide solution (160 µg/100 ml) for 10 minutes and washed with water several times. The purity and concentration of phagemid DNAs extracted from bands under UV light were determined.

(12) PCR for DNA Sequencing

Tertiary distilled water was added to 1 µg of the phagemid DNAs containing the gene of the 20 kDa protein obtained in (11) to a total volume of 10 µl. The resultant solution was mixed with 8 µl of a DNA sequencing solution (final concentration 3.2 pmole/µl) using a DNA sequencing kit including a Rhodamine terminator cycle sequencing ready reaction mixture (Perkin Elmer) containing T3 (SEQ ID NO: 8) and T7 (SEQ ID NO: 9) universal primers capable of binding the 3'- and 5'-ends of the phagemid DNAs. Mineral oil was dropwise added thereto and PCR was performed as follows: 24 cycles of 96° C. for 30 seconds, 50° C. for 15 seconds, and 60° C. for 4 minutes. Then, DNA samples were purified by a spin column, dried on a speed-vac, dissolved in 3 µl of a (deionized formamide:blue dextran=5:1) solution, heated to 95° C. for 2 minutes, and loaded on an automatic sequencer.

(13) DNA Sequence Analysis of 20 kDa PGN-Recognition Protein

A DNA sequence analysis of the 20 kDa PGN-recognition protein was performed using a dideoxy chain termination method developed by Sanger using a commercially available DNA sequencing kit (Rhodamine terminator cycle sequencing ready reaction, Perkin Elmer). The sequence analysis results showed that a polynucleotide encoding a *Tenebrio molitor* larval PGN-recognition protein had a nucleotide sequence as set forth in SEQ ID NO: 1.

(14) Analysis of Gene Sequence and Amino Acid Sequence of 20 kDa PGN-Recognition Protein After the primary screening, positive plaques appeared on all of the 20 plates.

After the secondary screening, 15 positive clones were obtained. The 1.5% agarose gel electrophoretic result showed that three of the 15 positive clones contained the gene of 20 kDa PGN-recognition protein. The sequence analysis of these three clones showed that the clones contained the same amino acid sequences as the partial amino acid sequences previously determined in Example 7. Each of these cDNA clones was identified as a 564-nucleotide open reading frame corresponding to 188 amino acids from the signal peptide to the stop codon (see FIG. 12).

The invention claimed is:

1. A separated and purified peptidoglycan-recognition protein having an amino acid sequence as set forth in SEQ ID NO: 1.

2. The separated and purified peptidoglycan-recognition protein of claim 1, which is encoded by a nucleotide sequence as set forth in SEQ ID NO: 2.

3. A peptidoglycan detection kit comprising the separated and purified peptidoglycan-recognition protein of claim 1.

* * * * *

SEQUENCE LISTING

<160> NUMBER OF SEQ ID NOS: 11

<210> SEQ ID NO 1
<211> LENGTH: 192
<212> TYPE: PRT
<213> ORGANISM: Tenebrio molitor

<400> SEQUENCE: 1

```
Met Leu Leu Ala Thr Ile Ala Arg Gly Val Tyr Gln Ile Ser Ala Leu
1               5                   10                  15

Ser Gly Ser Thr Ile Pro Arg Ile Cys Pro Glu Ile Ile Ser Arg Thr
            20                  25                  30

Arg Trp Gly Ala Arg Thr Pro Leu Glu Val Asp Tyr Ser Leu Ile Pro
        35                  40                  45

Ile Glu Asn Val Val His His Thr Val Thr His Thr Cys Asp Ser
    50                  55                  60

Glu Ser Glu Cys Ala Thr Leu Leu Arg Asn Val Gln Asn Phe His Met
65                  70                  75                  80

Glu Asn Leu Glu Phe His Asp Ile Gly Tyr Asn Phe Leu Val Ala Gly
                85                  90                  95

Asp Gly Gln Ile Tyr Glu Gly Ala Gly Trp His Lys Val Gly Ala His
            100                 105                 110

Thr Arg Gly Tyr Asn Thr Arg Ser Leu Gly Leu Ala Phe Ile Gly Asn
        115                 120                 125

Phe Thr Ser Gln Leu Pro Val Gln Lys Gln Leu Lys Val Ala Lys Asp
    130                 135                 140

Phe Leu Gln Cys Gly Val Glu Leu Gly Glu Leu Ser Lys Asn Tyr Lys
```

```
                145                 150                 155                 160
Leu Phe Gly Ala Arg Gln Val Ser Ser Thr Ser Ser Pro Gly Leu Lys
                165                 170                 175
Leu Tyr Arg Glu Leu Gln Asp Trp Pro His Phe Thr Arg Ser Pro Pro
            180                 185                 190

<210> SEQ ID NO 2
<211> LENGTH: 564
<212> TYPE: DNA
<213> ORGANISM: Tenebrio molitor

<400> SEQUENCE: 2
atgcgaggtg tgtatcaaat ttcggctctc tcaggttcta cgataccaag aatatgtcct      60
gaaattatta gtcggacaag atgggggggcg agaactccat tagaagtgga ttattcttta    120
attcccattg aaaatgttgt tgttcatcat actgtaactc atacatgcga ctcggaaagc     180
gaatgtgcaa ctcttttgag aaatgttcag aattttcaca tggaaaactt agaatttcat    240
gacataggat acaacttttt ggttgcaggt gacggacaaa tatacgaagg agcgggttgg    300
cataaagttg gagcgcatac cagaggctac aatacaagat ccttgggatt agcctttatt    360
ggcaacttca caagccaact accagtccaa aaacagctta agttgctaa agattttctt     420 caatgcggag ttgaactggg agaattaagt aaaaattata aattatttgg agcacgccaa    480
gtgagttcga caagcagccc tggactgaaa ctctaccgtg aactgcaaga ttggccccat    540
ttcaccagat ctcctcctaa ataa                                           564

<210> SEQ ID NO 3
<211> LENGTH: 23
<212> TYPE: PRT
<213> ORGANISM: Tenebrio molitor

<400> SEQUENCE: 3

Leu Ser Gly Ser Thr Ile Pro Arg Ile Cys Pro Glu Ile Ile Ser Arg
1               5                   10                  15

Thr Arg Trp Gly Ala Arg Thr
            20

<210> SEQ ID NO 4
<211> LENGTH: 14
<212> TYPE: PRT
<213> ORGANISM: Tenebrio molitor

<400> SEQUENCE: 4

Asp Phe Leu Gln Cys Gly Val Glu Leu Gly Glu Leu Ser Lys
1               5                   10

<210> SEQ ID NO 5
<211> LENGTH: 19
<212> TYPE: PRT
<213> ORGANISM: Tenebrio molitor

<400> SEQUENCE: 5

Asn Tyr Lys Leu Phe Gly Ala Arg Gln Val Ser Ser Thr Ser Ser Pro
1               5                   10                  15

Gly Leu Lys

<210> SEQ ID NO 6
<211> LENGTH: 17
<212> TYPE: PRT
<213> ORGANISM: Tenebrio molitor
```

```
<400> SEQUENCE: 6

Leu Tyr Arg Glu Leu Gln Asp Trp Pro His Phe Thr Arg Ser Pro Pro
1               5                   10                  15
Lys

<210> SEQ ID NO 7
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 7
gayttyytnc artgyggngt ng                                            22

<210> SEQ ID NO 8
<211> LENGTH: 20
<212> TYPE: DNA
<213> ORGANISM: Artificial Sequence
<220> FEATURE:
<223> OTHER INFORMATION: T3 primer

<400> SEQUENCE: 8
aattaaccct cactaaaggg                                               20

<210> SEQ ID NO 9
<211> LENGTH: 20
<212> TYPE: DNA
<213> ORGANISM: Artificial Sequence
<220> FEATURE:
<223> OTHER INFORMATION: T7 primer

<400> SEQUENCE: 9
taatacgact cactataggg                                               20

<210> SEQ ID NO 10
<211> LENGTH: 858
<212> TYPE: DNA
<213> ORGANISM: Tenebrio molitor

<400> SEQUENCE: 10
gaactcctgc ggtggcggcc gctctagact actggatccc ccgggctgca ggaattcggc    60
acgaggtgtg tatcaaattt cggctctctc aggttctacg ataccaagaa tatgtcctga   120
aattattagt cggacaagat gggggcgag aactccatta gaagtggatt attctttaat   180
tcccattgaa aatgttgttg ttcatcatac tgtaactcat acatgcgact cggaaagcga   240
atgtgcaact cttttgagaa atgttcagaa ttttcacatg gaaaacttag aatttcatga   300
cataggatac aacttttggg ttgcaggtga cggacaaata tacgaggag cgggttgca   360 taaagttgga gcgcatacca gaggctacaa tacaagatcc ttgggattag cctttattgg   420
caacttcaca agccaactac cagtccaaaa acagcttaaa gttgctaaag attttcttca   480
atgcggagtt gaactgggag aattaagtaa aaattataaa ttatttggag cacgccaagt   540
```

```
gagttcgaca agcagccctg gactgaaact ctaccgtgaa ctgcaagatt ggccccattt    600
caccagatct cctcctaaat aaattcatca acagttcaac aattgttgta ttttatatta    660
ttgttttatg tcattaaata atcgaattat cgggcggagg ccaaaaaata gacataaaat    720
acacgcaggc ataaaaacac agacaaacaa aaaaattttt ctcgagtggg agcccggtac    780
caattacgcc ctatagtgag tcgtataaca gattcactgg gcggtcgttt tacagtgcgt    840
gactgggaaa aacccttg                                                   858

<210> SEQ ID NO 11
<211> LENGTH: 187
<212> TYPE: PRT
<213> ORGANISM: Tenebrio molitor

<400> SEQUENCE: 11

Ala Arg Gly Val Tyr Gln Ile Ser Ala Leu Ser Gly Ser Thr Ile Pro
1               5                   10                  15

Arg Ile Cys Pro Glu Ile Ile Ser Arg Thr Arg Trp Gly Ala Arg Thr
                20                  25                  30

Pro Leu Glu Val Asp Tyr Ser Leu Ile Pro Ile Glu Asn Val Val Val
            35                  40                  45

His His Thr Val Thr His Thr Cys Asp Ser Glu Ser Glu Cys Ala Thr
        50                  55                  60

Leu Leu Arg Asn Val Gln Asn Phe His Met Glu Asn Leu Glu Phe His
65                  70                  75                  80

Asp Ile Gly Tyr Asn Phe Leu Val Ala Gly Asp Gly Gln Ile Tyr Glu
                85                  90                  95

Gly Ala Gly Trp His Lys Val Gly Ala His Thr Arg Gly Tyr Asn Thr
            100                 105                 110

Arg Ser Leu Gly Leu Ala Phe Ile Gly Asn Phe Thr Ser Gln Leu Pro
        115                 120                 125

Val Gln Lys Gln Leu Lys Val Ala Lys Asp Phe Leu Gln Cys Gly Val
130                 135                 140

Glu Leu Gly Glu Leu Ser Lys Asn Tyr Lys Leu Phe Gly Ala Arg Gln
145                 150                 155                 160

Val Ser Ser Thr Ser Ser Pro Gly Leu Lys Leu Tyr Arg Glu Leu Gln
                165                 170                 175

Asp Trp Pro His Phe Thr Arg Ser Pro Pro Lys
            180                 185
```